United States Patent

Mase et al.

[11] Patent Number: 5,140,046
[45] Date of Patent: Aug. 18, 1992

[54] PHENYLENE DERIVATIVES, COMPOSITIONS AND USE

[75] Inventors: Toshiyasu Mase, Chiba; Kiyoshi Murase, Saitama; Hiromu Hara, Saitama; Kenichi Tomioka, Saitama, all of Japan

[73] Assignee: Yamanouchi Pharmaceutical Co., Ltd., Tokyo, Japan

[21] Appl. No.: 567,159

[22] Filed: Aug. 13, 1990

Related U.S. Application Data

[62] Division of Ser. No. 899,218, Aug. 15, 1986, Pat. No. 4,994,479.

[30] Foreign Application Priority Data

Apr. 3, 1985 [JP] Japan ................. 60-70566
Dec. 26, 1985 [JP] Japan ................. 60-297096

[51] Int. Cl.$^5$ ................. A61K 31/19; C07C 233/81
[52] U.S. Cl. ................. 514/563; 562/455; 562/465; 562/471
[58] Field of Search ................. 562/455, 465, 471; 514/563

[56] References Cited

U.S. PATENT DOCUMENTS 4,026,896  5/1977  Harita et al. ................. 514/563
4,322,439  5/1982  Klumm et al. ................. 562/455

OTHER PUBLICATIONS

Drain et al., J. Pharm. Pharmol, 22 (1970) pp. 684–693.

Primary Examiner—Robert W. Ramsuer
Assistant Examiner—M. S. H. Gabilan
Attorney, Agent, or Firm—Burgess, Ryan & Wayne

[57] ABSTRACT

Novel phenylene derivatives shown by the general formula

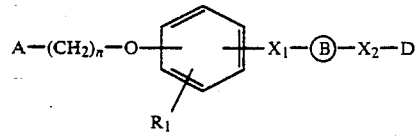

where A represents a hydrogen atom, a phenyl group or a phenoxy group, n represents an integer of 3 to 10, $R_1$ represents a hydrogen atom or a lower alkoxy group, $X_1$ represents —CH$_2$CH$_2$—, —CH=CH—, —CONH—, Ⓑ represents

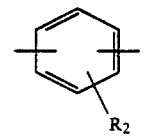

wherein $R_2$ represents a hydrogen atom, a halogen atom, a nitro group, etc.),

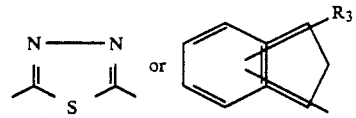

(wherein $R_3$ represents a hydrogen atom, a hydroxyl group or a lower alkoxy group), $X_2$ represents —CH=CH—, —CH$_2$CH$_2$—, etc. and D represents a carboxy group, a lower alkoxycarbonyl group or

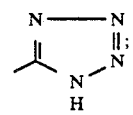

which are useful as drugs, particularly SRS-A(slow reacting substance of anaphylaxis) antagonist, i.e. they are useful as prophylaxis and treatment for various allergic diseases (e.g. bronchial asthma, allergic rhinitis, urticaria) or, ischemic heart diseases, inflammation, etc. induced by SRS-A.

17 Claims, No Drawings

PHENYLENE DERIVATIVES, COMPOSITIONS AND USE

This is a division of application Ser. No. 899,218, filed Aug. 15, 1986 now U.S. Pat. No. 4,994,479.

DESCRIPTION

1. Field of the Invention

The present invention relates to novel phenylene derivatives useful as drugs, particularly SRS-A (slow reacting substance of anaphylaxis) antagonists. (Means for solving the problems).

2. Description of the Invention

The compounds of the present invention are phenylene derivatives represented by general formula (I) described below.

Compounds represented by general formula (I) or pharmaceutically acceptable salts thereof:

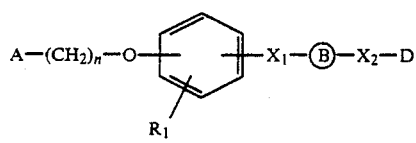

wherein symbols represent:

A: a hydrogen atom, a phenyl group or a phenoxy group, n: an integer of 3 to 10

$R_1$: a hydrogen atom or a lower alkoxy group, $X_1$: a group shown by —$CH_2CH_2$—, —CH=CH—, —$CH_2$—$Y_1$— (wherein $Y_1$: —O—, —S— or —NH—), —$Y_1$—$CH_2$—, —CO—$Y_2$— (wherein $Y_2$: —NH—, —$CH_2$—$Y_1$— or —$Y_1$—$CH_2$—) or —$Y_2$—CO—.

Ⓑ: a group represented by:

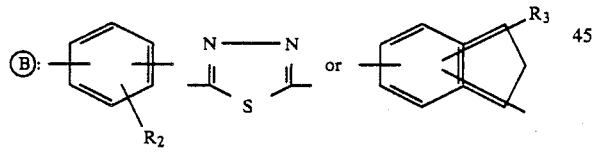

wherein:

$R_2$: a hydrogen atom, a halogen atom, a nitro group, a hydroxy group, a lower alkoxy group, a carboxy group, a cyano group, an oxaloamido group (—NHCOCOOH), a lower alkoxycarbonyl group, a lower alkyl group, a hydroxy-lower alkyl group, a lower alkoxy-lower alkyl group, a carboxy-lower alkyl group, a lower alkoxycarbonyl-lower alkyl group, a carboxy-lower alkylthio-lower alkyl group, a lower alkoxycarbonyl-lower alkylthio-lower alkyl group, a halo-lower alkyl group, a carboxyl-lower alkoxy group, a lower alkoxycarbonyl-lower alkoxy group, a lower alkanoyl-lower alkoxy group, a lower alkoxycarbonyl-lower alkoxy group, a lower alkanoyl group or a group represented by the formula:

(wherein $R_4$ and $R_5$, which may be the same or different, each represents a hydrogen atom, a lower alkyl group, a carboxy-lower alkyl group, a lower alkoxycarbonyl-lower alkyl group, a lower alkanoyl group, a carboxy-lower alkanoyl group, a lower alkoxycarbonyl-lower alkanoyl group, a substituted or unsubstituted phenyl-lower alkoxycarbonyl-lower alkanoyl group, a carbamoyl group, a lower alkoxy oxalyl group or a mono- or di-lower alkylaminocarbonyl group), $R_3$: a hydrogen atom, a hydroxy group or a lower alkoxy group, $X_2$: a group represented by —CH=CH— or —$Y_3$—$Y_4$— (wherein $Y_3$: a single bond, —O—, —S— or —NH—; $Y_4$: an alkylene group having 1 to 6 carbon atoms which may be interrupted by a sulfur atom), D: a carboxy group, a lower alkoxycarbonyl group or a group represented by:

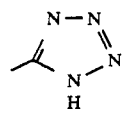

provided that Ⓑ is:

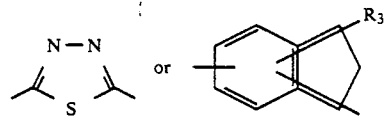

or D is:

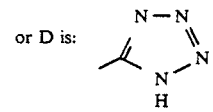

when A is a hydrogen atom.

Definitions of the aforesaid general formula (I) and general formulae later described, and preferred specific examples thereof, are described in detail below.

The term "lower" as used throughout the present specification refers to a straight or branched carbon chain having 1 to 6 carbon atoms, unless otherwise indicated.

Accordingly, the "lower alkyl group" includes a methyl group, an ethyl group, a propyl group, an isopropyl group, a butyl group, an isobutyl group, a sec-butyl group, a tert-butyl group, a pentyl group, an isopentyl group, a hexyl group, an isohexyl group, etc. Also the "lower alkoxy" and "lower alkoxy group" include a methoxy group, an ethoxy group, a propoxy group, an isopropoxy group, a butoxy group, an isobutoxy group, a sec-butoxy group, a tert-butoxy group, a pentyloxy group, an isopentyloxy group, a hexyloxy group, an isohexyloxy group, etc.

The "alkylene group having 1 to 6 carbon atoms which may be interrupted with a sulfur atom" for $Y_4$ includes a methylene group, an ethylene group and the aforesaid alkylene group having 3 to 6 carbon atoms; in addition thereto, includes these alkylene groups interrupted by one sulfur atom at an optional position thereof, specifically $-CH_2-S-CH_2-$, $-(CH_2)_2-S-CH_2-$, $-(CH_2)_3-S-CH_2-$, $-(CH_2)_4-S-CH_2-$, $-(CH_2)_2-S-(CH_2)_3-$, $-CH_2-S-(CH_2)_4-$, $-CH_2-CH(CH_3)-CH_2-S-CH_2-$, etc.

Specific examples of the "group shown by formula: $-CH_2-Y_1-$ or $-Y_1-CH_2-$" for $X_1$ include a methyleneoxy group ($-CH_2-O-$), a methylenethio group ($-CH_2-S-$), a methylenimino group ($-CH_2-NH-$), an oxymethylene group ($-O-CH_2-$), a thiomethylene group ($-S-CH_2-$), an iminomethylene group ($-NH-CH_2-$), etc.

Specific examples of the "group shown by formula: $-CO-Y_2-$ or $-Y_2-CO-$" for $X_1$ include a carbonylimino group ($-CONH-$), a carbonylmethyleneoxy group ($-COCH_2-O-$), a carbonylmethylenethio group ($-COCH_2-S-$), a carbonylmethyleneimino group ($-COCH_2-NH-$), an iminocarbonyl group ($-NHCO-$), a methyleneoxycarbonyl group ($-CH_2-O-CO-$), a methylenethiocarbonyl group ($-CH_2-S-CO-$), a methyleneiminocarbonyl group ($-CH_2-NH-CO-$), an oxymethylenecarbonyl group ($-O-CH_2-CO-$), a thiomethylenecarbonyl group ($-S-CH_2-CO-$), an iminomethylenecarbonyl group ($-NH-CH_2-CO-$), a carbonyloxy group ($-CO-O-$), a carbonylthio group ($-CO-S-$), an oxycarbonyl group ($-O-CO-$), a thiocarbonyl group ($-S-CO-$), etc.

Specific examples of the "lower alkanoyl group" for $R_2$, $R_4$ or $R_5$ include a formyl group, an acetyl group, a propionyl group, a butyryl group, an isobutyryl group, a valeryl group, an isovaleryl group, etc.; specific examples of the "substituted phenyl-lower alkoxycarbonyl-lower alkanoyl group" include p-methoxybenzyloxycarbonylacetyl group, etc.; and specific examples of the "lower alkoxy oxalyl group" include a methoxy oxalyl group, an ethoxy oxalyl group, etc.

Specific examples of the "group shown by formula: $-Y_3-Y_4-$" for $X_2$ include a methylene group ($-CH_2-$), an ethylene group ($-CH_2-CH_2-$), a tetramethylene group ($-(CH_2)_4-$), a pentamethylene group ($-(CH_2)_5-$), a methylenethiomethylene group ($-CH_2-S-CH_2-$), an oxymethylene group ($-OCH_2-$), an oxyethylene group ($-O-CH_2CH_2-$), an oxypropylene group ($-O-CH_2-CH_2-CH_2-$), an oxypropylenethiomethylene group ($-O-CH_2CH_2CH_2-S-CH_2-$), a thiomethylene group ($-S-CH_2-$), a thioethylene group ($-S-CH_2CH_2-$), a thiopropylene group ($-S-CH_2CH_2CH_2-$), a thioethylenethiomethylene group ($-S-CH_2CH_2-S-CH_2-$), an iminomethylene group ($-NHCH_2-$), an iminoethylene group ($-NHCH_2CH_2-$), an iminoethylenethioethylene group ($-NH-CH_2CH_2-S-CH_2CH_2-$), etc.

The compounds of general formula (I) described above include optical isomers based on the presence of an asymmetric carbon and cis- and trans-stereoisomers based on the presence of the alkenyl group, etc. The compounds of the present invention are encompassed to include isolated isomers thereof and mixtures thereof Some of the compounds of the present invention form salts thereof. The present invention also includes salts of the compounds of general formula (I) described above. Examples of such salts are salts with inorganic bases such as sodium, potassium, etc.; salts with organic bases such as ethylamine, propylamine, diethylamine, triethylamine, morpholine, piperidine, N-ethylpiperidine, diethanolamine, cyclohexylamine, etc.; salts with basic amino acids such as lysine, ornithine, etc.; ammonium salts; salts with mineral acids such as hydrochloric acid, sulfuric acid, phosphoric acid, hydrobromic acid, etc.

The desired compounds of the present invention exhibit a potent antagonistic action on SRS-A.

It is generally considered that in allergic asthma and other atopic diseases of human or anaphylactic shock in animals, various chemical mediators are released from the lung and other tissues and cause difficulties in the living body, such as contraction of smooth muscles, e.g., bronchi, pulmonary artery, etc., and enhancement of vascular permeability in the skin. As such chemical mediators, there are histamine and SRS-A. Histamine plays an important role in guinea pig anaphylactic shock but not in allergic asthma in humans [Eiser, Pharmacol. Ther., 17, 239–250 (1982)]; whereas a number of evidences suggest that SRS-A is the most important chemical mediator of allergic asthma in humans [Brocklehurst, J. Physiol., 151, 416–435 (1960); Austen and Orange, Am. Rev. Resp. Dis., 112, 423–436 (1975); Adams and Lichtenstein, J. Immunol., 122, 555–562 (1979)].

The development of medicaments for prophylaxis, elimination and alleviation of hypersensitive reactions was performed, aiming at inhibiting the production and release of such chemical mediators or antagonizing the action of these chemical mediators. As an inhibitor of histamine release, disodium cromoglycate is well known and as an inhibitor of actions induced by histamine, various anti-histaminics are commercially available. On the other hand, SRS-A is known as a slow reactive and long acting chemical mediator while histamine is a rapid acting and short acting chemical mediator. It has recently been clarified that SRS-A is a mixture of Leukotrienes $C_4$, $D_4$ and $E_4$, the structure of which have been determined by Samuelsson. SRS-A, namely, Leukotrienes are metabolites of polyvalent unsaturated fatty acids (in particular, arachidonic acid) with lipoxygenase and it has been reported that SRS-A has various activities such as acceleration of mucus secretion, reduction of mucociliary movement, coronary artery contraction, reduction of cardiac contraction, etc., in addition to the aforesaid action as chemical mediator in immediate hypersensitivity reactions. Accordingly, it has been desired to develop medicaments capable of inhibiting the production and release of SRS-A or antagonizing the effects of SRS-A.

The present inventors have extensively investigated medicaments capable of inhibiting the production and release of SRS-A or medicaments capable of antagonizing the effects of SRS-A. As a result, they have found that the compounds (I) of the present invention strongly antagonize SRS-A and have accomplished the present invention.

The compounds (I) of the present invention are useful as prophylaxis and treatment for various allergic diseases (for example, bronchial asthma, allergic rhinitis, urticaria) or, ischemic heart diseases, inflammation, etc. induced by SRS-A since the compounds strongly antagonize SRS-A as described above.

Further some of the compounds of the present invention exhibit an activity similar to that of SRS-A. It can be expected that such compounds having the SRS-A agonist activity can be used in treatment for intestinal tube paralysis and also effective as reagents for investigations of anti-SRS-A agents or SRS-A antagonists; in place of Leukotrienes that have been heretofore difficult to acquire in a stable form.

The compounds (I) of the present invention can be orally or perenterally administered safely as medical compositions [for example, tablets, capsules, powders, granules, pills, ointments, syrups, injections, inhalation, sapositories] as they are, or by mixing with known pharmaceutically acceptable carriers, excipients, etc. Dose may vary depending upon object to be administered, route for administration, condition, etc. but a daily dose is generally 0.1 to 500 mg, preferably 1 to 200 mg, for adult. The dose is orally or perenterally administered twice or three times a day.

The compounds of the present invention can be prepared, for example, by processes shown by the following reaction equations:

Process 1:

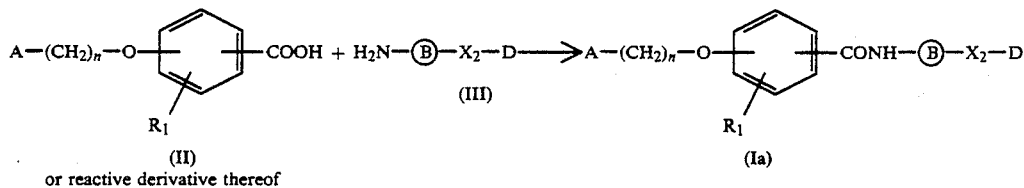

(II)
or reactive derivative thereof (III)

(Ia)

Process 2:

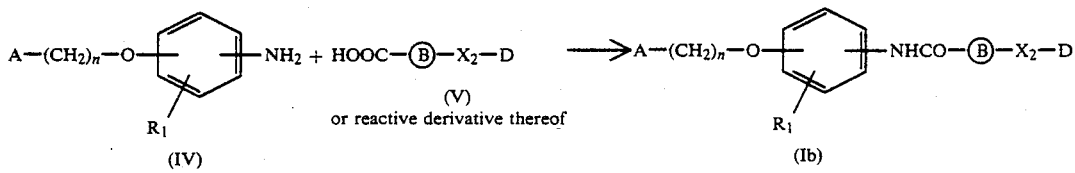

(IV)

(V)
or reactive derivative thereof (Ib)

Process 3:

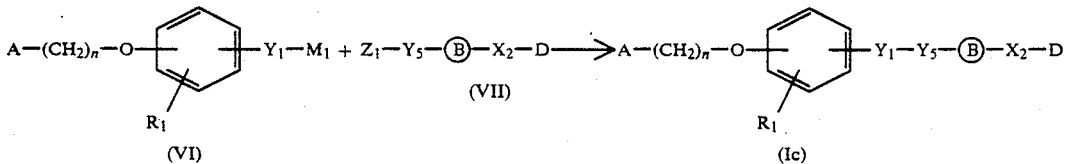

(VI)

(VII)

(Ic)

Process 4:

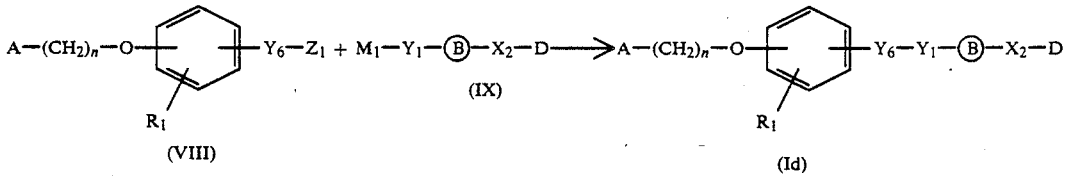

(VIII)

(IX)

(Id)

Process 5:

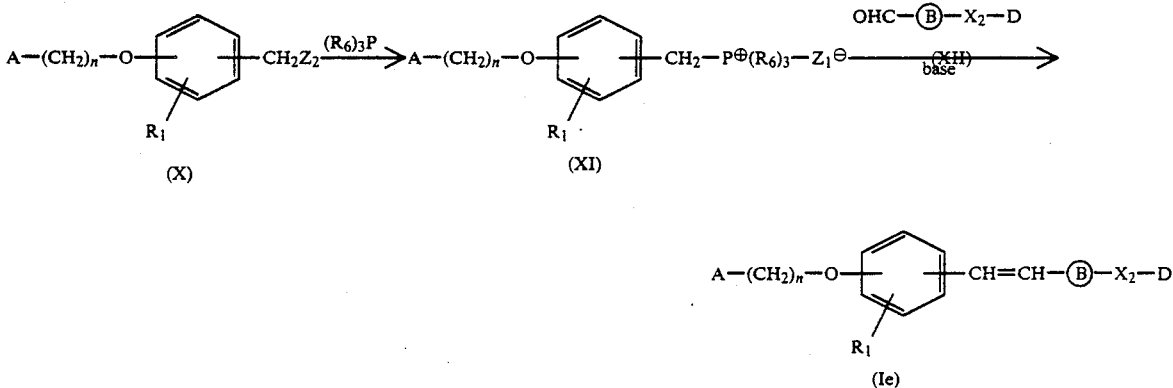

(X)

(XI)

(Ie)

Process 6:

-continued

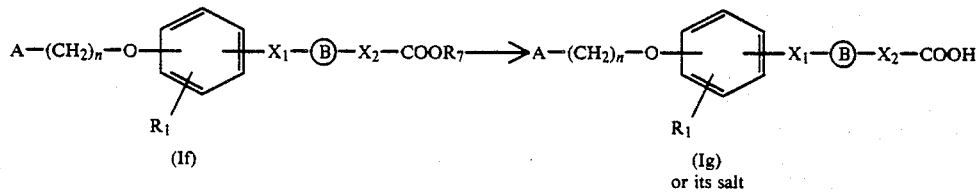

(If) → (Ig) or its salt

Process 7:

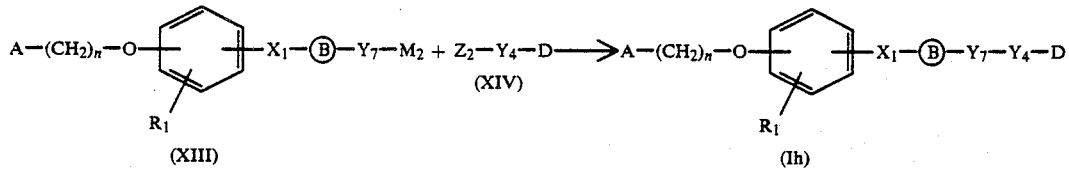

(XIII) (XIV) (Ih)

Process 8:

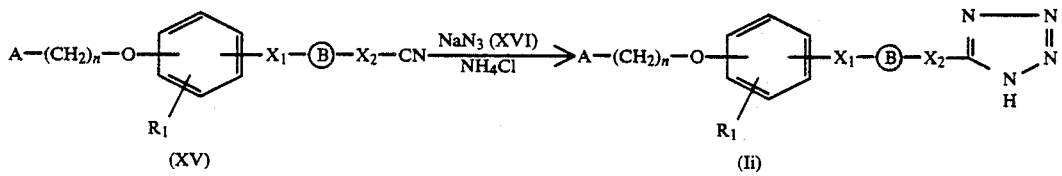

(XV) (Ii)

Process 9:

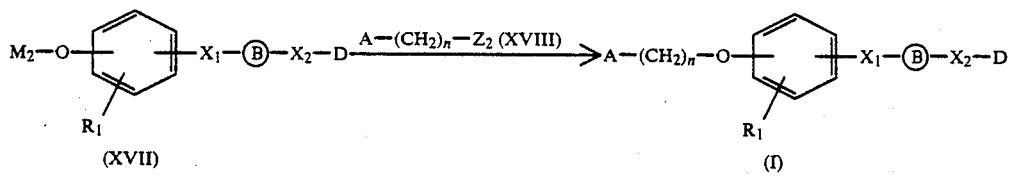

(XVII) (XVIII) (I)

wherein A, n, $R_1$, $X_1$,-(B)- $X_2$, $Y_1$ and D have the same meaning as described hereinabove and the other symbols have the following meaning:

$M_1$: a hydrogen atom or an alkali metal atom when $Y_1$ is an oxygen atom or a sulfur atom and when $Y_1$ is an imino group, a hydrogen atom;

$Z_1$: a halogen atom or a sulfonyloxy group;

$Y_5$: a methylene group or a methylenecarbonyl group (—$CH_2CO$—);

$Y_6$: a methylene group or a carbonylmethylene group (—$COCH_2$—);

$Z_2$: a halogen atom;

$R_6$: a phenyl group or a butyl group;

$R_7$: a lower alkyl group or a lower alkoxyphenyl-lower alkyl group;

$Y_7$: an oxygen atom or a sulfur atom;

$M_2$: a hydrogen atom or an alkali metal atom.

Examples of the alkali metal atom shown by $M_1$ or $M_2$ include a sodium atom, a potassium atom. Examples of the halogen atom shown by $Z_1$ or $Z_2$ include an iodine atom, a bromine atom, a chlorine atom, etc. As the sulfonyloxy group, a toluenesulfonyloxy group, a benzenesulfonyloxy group, etc. are preferably used.

Process 1

In the compounds of the present invention, Compound (Ia) wherein $X_1$ is a carbonylimino group (—CONH—) is prepared by reacting a substituted benzoic acid shown by general formula (II) or a reactive derivative thereof with an amino compound shown by general formula (III).

As the reactive derivatives of Compound (II), there are acid halides such as acid chlorides, acid bromides, etc.; acid azides; activated esters with N-hydroxybenztriazole or N-hydroxysuccinimide; symmetric acid anhydrides; alkyl carbonate mixed acid anhydride, mixed acid anhydrides with p-toluenesulfonic acid; etc.

In the case where Compound (II) is reacted with a free carboxylic acid, it is advantageous to perform the reaction in the presence of a condensing agent such as dicyclohexylcarbodiimide, 1,1'-carbonyldiimidazole, etc.

The reaction is performed using Compound (II) or a reactive derivative thereof and Compound (III) in an almost equimolar amount or in a slightly excessive amount of one of them, in an organic solvent inert to the reaction, for example, pyridine, tetrahydrofuran, dioxane, ether, benzene, toluene, xylene, methylene chloride, dichloroethane, chloroform, dimethylformamide, ethyl acetate, acetonitrile, or the like.

Depending upon kind of the reactive derivative, it is sometimes advantageous for smooth performance of the reaction to add a base such as triethylamine, pyridine, picoline, lutidine, N,N-dimethylaniline, potassium carbonate, sodium hydroxide, etc. Pyridine can also be used as the solvent.

The reaction temperature may vary depending upon kind of the reactive derivative but is not particularly limited.

Process 2

In the compounds of the present invention, Compound (Ib) wherein $X_1$ is an iminocarbonyl group (—NHCO—) is prepared by reacting a substituted aniline shown by general formula (IV) with a carboxylic acid shown by general formula (V) or a reactive derivative thereof.

The reaction conditions are almost the same as in Process 1.

Process 3

In the compounds of the present invention, the group of Compounds (Ic) wherein $X_1$ is $-Y_1-CH_2-$ i.e., $-O-CH_2-$, $-S-CH_2-$ or $-NH-CH_2-$ can be produced by reacting a substituted phenol or substituted phenylmercaptan or an alkali metal-substituted compound thereof or a substituted aniline shown by general formula (VI) with a halogen compound or a sulfonate compound shown by general formula (VII).

The reaction is performed using Compound (VI) and Compound (VII) in an almost equimolar amount or in an excess amount of either compound in an organic solvent such as dimethylformamide, dimethylsulfoxide, methanol, ethanol, propanol, acetone, methyl ethyl ketone, tetrahydrofuran, chloroform, dioxane, benzene, toluene, xylene, dichloromethane, dichloroethane, etc.

The reaction is conducted, if necessary, in the presence of a base. Preferred examples of such bases include potassium carbonate, Triton B, potassium hydroxide, sodium hydride, sodium carbonate, pyridine, picoline, N,N-dimethylaniline, N-methylmorpholine, trimethylamine, triethylamine, etc.

The reaction temperature is not particularly limited but generally set at room temperature or higher.

Process 4

In the compounds of the present invention, the group of Compound (Id) wherein $X_1$ is $-CH_2-Y_1-$, i.e., $-CH_2O-$, $-CH_2S-$, or $-CH_2NH-$ can be produced by reacting a halogen compound or sulfonate compound shown by general formula (VIII) with a hydroxy- or mercaptan-compound or an alkali metal-substituted compound or an amine compound shown by general formula (IX).

The reaction conditions are almost identical with those of Process 3.

Process 5

In the compounds of the present invention, Compound (Ie) wherein $X_1$ is a vinylene group ($-CH=CH-$) can be produced by reacting a substituted benzyl halide shown by general formula (X) with triphenyl(or tributyl)phosphine, then reacting the resulting substituted benzyltriphenylphosphonium halide with a base such as n-butyl lithium, an alkali metal amide, an alkali metal alkoxide, methylsulfinylmethylide sodium salt, etc., and finally reacting the resulting substituted benzyltriphenylphosphorane with an aldehyde shown by general formula (XII).

The reaction at the former stage may proceed in the absence of any solvent but generally performed in an organic solvent such as benzene, toluene, xylene, etc. The reaction temperature is not particularly limited.

The reaction at the latter stage is performed in the organic solvent used in the reaction at the former stage or in a solvent such as tetrahydrofuran, ether, dimethoxyethane, dimethylsulfoxide, alcohol, etc. The reaction temperature is not particularly limited.

Process 6

In the compounds of the present invention, Compound (Ig) wherein D is a carboxy group can be produced by removing an ester residue from the corresponding ester shown by general formula (If).

In the reaction, a conventional manner of either hydrolyzing in the presence of a base such as sodium carbonate, sodium hydroxide, etc., or treating with an acid such as trifluoroacetic acid, hydrochloric acid, etc. is applicable.

Process 7

In the compounds of the present invention, Compound (Ih) wherein $X_2$ is $-Y_7-Y_4-$, i.e., $-O-Y_4-$ or $-S-Y_4-$ can be produced by reacting a hydroxy- or mercapto-compound or an alkali metal-substituted compound shown by general formula (XIII) with a substituted alkyl halide shown by general formula (XIV).

The reaction conditions are almost identical with those of Processes 3 and 4.

Process 8

In the compounds of the present invention, Compound (Ii) wherein D is a 1H-1,2,3,4-tetrazol-2-yl group can be produced by reacting a nitrile compound shown by general formula (XV) with sodium azide in the presence of ammonium chloride.

The reaction is performed with heating in an organic solvent such as dimethylformamide, dimethylsulfoxide, etc.

Process 9

The compounds of the present invention can be produced by reacting a hydroxy compound or a metal-substituted compound shown by general formula (XVII) with a substituted alkyl halide shown by general formula (XVIII). The reaction conditions are almost identical with those of Processes 3 and 4.

In the case where Compound (I) contains a vinylene group, the vinylene group can also be reduced to the corresponding alkyl group by catalytic reduction using palladium-carbon, etc. in a conventional manner.

Ⓑ of the desired compounds is

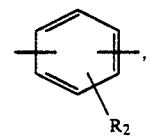

and the compound wherein $R_2$ is a formyl group can be obtained by elimination of the protecting group of a compound wherein $R_2$ is:

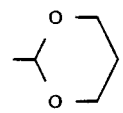

(protecting group).

Further conversion of one product into another product can be performed in a conventional manner. For example, a compound wherein $R_2$ is:

wherein $R_4$ and $R_5$ are both not a hydrogen atom, can be obtained by alkylation, acylation, etc. of a compound wherein $R_2$ is an amino group; a compound wherein $R_2$ is a halo-lower alkyl group by halogenation of a compound wherein $R_2$ is a hydroxy-lower alkyl group; a compound wherein $R_2$ is a hydroxymethyl group by reduction of a compound wherein $R_2$ is a formyl group; a compound wherein $R_2$ is a lower alkoxy-lower alkyl group by lower alkoxylation of a compound wherein $R_2$ is a halo-lower alkyl group; a compound wherein $R_2$ is a lower alkoxycarbonyl-lower alkylthio-lower alkyl group by lower alkoxycarbonyl-lower alkylsulfenylation of a compound wherein $R_2$ is a halo-lower alkyl group. These conversion modes are described in the examples later in detail.

The compounds of the present invention produced by these various processes can be isolated and purified by applying thereto chemical procedures generally used in the art such as extraction, recrystallization, column chromatography, etc.

(1) Inhibition of SRS-A- and LTD$_4$-induced contractions of guinea-pig ileum and trachea Method Male Hartley guinea-pigs, weighing 500 to 700 g were sacrificed by a blow on the head. The ileum and tracheal strips prepared according to the method of Constantine (1965) were suspended with 1.0 g tension in an organ bath containing 10 ml of Tyrode solution equilibrated with a mixture of 95% $O_2$ and 5% $CO_2$ at 37° C. The tissues were equilibrated for 60 minutes; during this period the Tyrode solution was replaced every 15 minutes and the loading tension was adjusted to 1.0 g. The developed tension of the tissues was measured isometrically with a strain gauge transducer, and recorded on a Recticorder. Both the contractile response of the ileum to submaximal concentration of SRS-A (derived from guinea-pig lung) and tracheal response to $10^{-8}$M LTD$_4$ were recorded in the absence and then the presence of various concentrations of test compounds. The incubation time of the compounds was 20 minutes.

Results

The compounds of the present invention, e.g., compounds of Examples 23, 10, 18, 42, 40, 41 and 39, showed potent anti-SRS-A activity in isolated guinea-pig ileum (Table 1). Further, compounds of Examples 23, 40 and 39 inhibited the contractions induced by LTD$_4$ in isolated guinea-pig trachea (Table 1).

TABLE 1

Anti-SRS-A and anti-LTD$_4$ effects of representative compounds of this invention in isolated guinea-pig ileum and trachea

| Example No. of compound | IC 50 (M) | |
|---|---|---|
| | Ileum a-SRS-A | Trachea a-LTD$_4$ |
| Ex. 23 | $4.4 \times 10^{-8}$ | $4.0 \times 10^{-7}$ |
| Ex. 10 | $1.8 \times 10^{-8}$ | — |
| Ex. 18 | $3.3 \times 10^{-8}$ | — |
| Ex. 42 | $8.1 \times 10^{-8}$ | — |
| Ex. 40 | $3.6 \times 10^{-9}$ | $5.7 \times 10^{-8}$ |

TABLE 1-continued

Anti-SRS-A and anti-LTD$_4$ effects of representative compounds of this invention in isolated guinea-pig ileum and trachea

| Example No. of compound | IC 50 (M) | |
|---|---|---|
| | Ileum a-SRS-A | Trachea a-LTD$_4$ |
| Ex. 41 | $7.4 \times 10^{-9}$ | — |
| Ex. 39 | $7.3 \times 10^{-9}$ | $2.5 \times 10^{-7}$ |

(2) Inhibition of LTD$_4$-enhanced vascular permeability in guinea-pigs

Method

Male Hartley guinea-pigs weighing 270 to 305 g, starved for 16 hours, were intradermally injected with 5 ng LTD$_4$ in a volume of 0.1 ml into two sites on the shaved back. In addition, 0.1 ml of vehicle was injected intradermally in each animal to see non-specific irritation. One ml of saline containing 1% Evans value was intravenously injected 2 minutes before LTD$_4$ injection. The leaked dye at the site of LTD$_4$ or vehicle injection was extracted according to the method of Harada et al. (1971) and measured photometrically at 620 nm. The LTD$_4$-induced skin reaction was expressed as a difference in the amount of dye between LTD$_4$ and vehicle. Test compounds were orally administered 30 minutes before LTD$_4$ injection.

Results

Compounds of Examples 23, 39 and 40 dose-dependently inhibited the LTD$_4$-enhanced vascular permeability in guinea-pigs; their ED$_{50}$ were 22.8, 36.1 and 5.5 mg/kg p.o., respectively. These results indicate that Compounds of Examples 23, 39 and 40 show potent anti-Leukotriene effect by oral route.

(3) Acute Toxicity in Rats

Male Fischer 344 rats 7 week old were used. Compounds of Examples 39 and 40 at 1000 mg/kg p.o. caused no toxic effect upon the rats during the observation period of 7 days.

References

Constantine, J. W., J. Pharm. Pharmacol., 17, 384 (1965)

Harada, M. et al., ibid., 23, 218 (1971)

Hereafter the present invention will be described in detail with reference to the examples below.

REFERENCE EXAMPLE 1

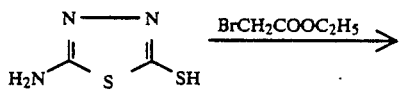

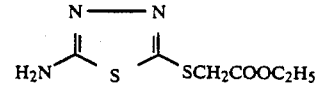

To a mixture of 3.9 g of 2-amino-5-mercapto-1,3,4-thiadiazole, 4.2 g of potassium carbonate and 50 ml of ethanol was gradually added 5 g of ethyl bromoacetate under ice cooling. Then, the mixture was stirred at room temperature for 3 hours. To the reaction mixture was added 200 ml of water followed by extraction with ethyl acetate. After washing with water, the extract was dried over anhydrous magnesium sulfate and the solvent was distilled off. The solid obtained was washed with toluene and dried to obtain 2.7 g of ethyl [(5-amino-1,3,4-thiadiazol-2-yl)thio]acetate.

Nuclear magnetic resonance spectra (CDCl₃, TMS, ppm) 1.25(3H, t, —CH₃), 3.90(2H, s, —CH₂—), 4.19(2H, q, —CH₂)

REFERENCE EXAMPLE 2

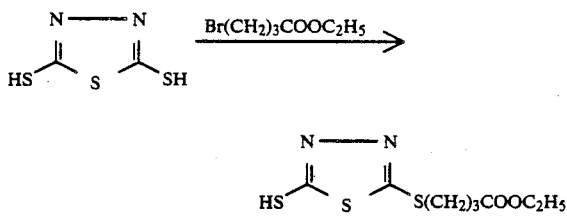

To a solution of 9.92 g of sodium hydroxide in 160 ml of methanol-water (10:1) was added 37.2 g of 2,5-dimercapto-1,3,4-thiadiazole to dissolve. Then 40 g of ethyl bromobutyrate was added to the solution followed by stirring for 3 hours. The reaction mixture was settled overnight. The formed solid was taken by filtration, washed with methanol-water (10:1) and dried under reduced pressure to obtain 41.5 g of ethyl 3-[(5-mercapto-1,3,4-thiadiazol-2-yl)thio]butyrate. Melting point: 107°~108° C.

REFERENCE EXAMPLE 3

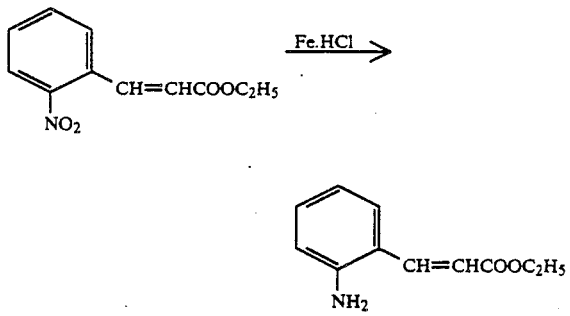

A mixture of 2.2 g of reduced iron, 0.5 ml of conc. hydrochloric acid and 2.5 ml of water was added to a solution of 2.2 g of ethyl o-nitrocinnamate in 30 ml of ethanol. After heating under reflux for 1 hour, insoluble matters were filtered off and the filtrate was concentrated under reduced pressure. An aqueous sodium hydrogen carbonate solution was added to the residue followed by extraction with toluene. After the extract was washed with water and dried, the solvent was distilled off to obtain 1.6 g of ethyl o-aminocinnamate as yellow crystals.

Nuclear magnetic resonance spectra (CDCl₃, TMS, ppm) 1.30(3H, t, —CH₃), 4.23(2H, q, —OCH₂—), 6.30(1H, d), 6.50–7.50(4H, m), 7.80(1H, d)

REFERENCE EXAMPLE 4

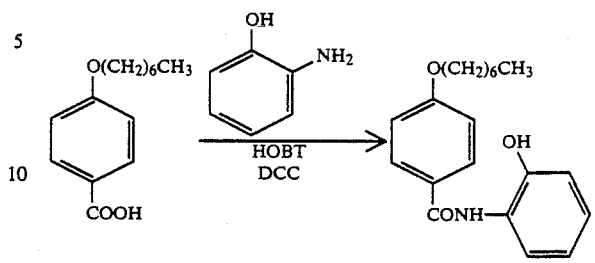

To a mixture of 4.7 g of p-heptyloxybenzoic acid, 2.7 g of 1-hydroxybenztriazole (HOBT) and 50 ml of tetrahydrofuran was added 4.2 g of dicyclohexylcarbodiimide (DCC) under ice cooling. After stirring at room temperature for 1 hour, 9 g of o-aminophenol was added to the mixture. The resulting mixture was stirred at room temperature overnight. Dicyclohexyl urea formed was filtered off and the filtrate was concentrated. The residue was dissolved in 500 ml of ethyl acetate. The solution was washed subsequently with diluted hydrochloric acid, a diluted sodium hydrogen carbonate solution and then water, dried over anhydrous magnesium sulfate and the concentrated under reduced pressure. The residue was applied to silica gel column chromatography (using 500 ml of silica gel), eluted with a toluene-ethyl acetate (1:1) mixture and further recrystallized from ethanol to obtain 5.6 g of p-heptyloxy-N-(o-hydroxyphenyl)benzamide.

Melting point: 131°~133° C.

REFERENCE EXAMPLES 5~7

In a manner similar to Reference Example 4, the following compounds were obtained.

Reference Example 5 m-Heptyloxy-N-(o-hydroxyphenyl)benzamide
Melting point: 108~109° C.

Reference Example 6 p-Heptyloxy-N-(m-hydroxyphenyl)benzamide
Melting point: 182~184° C.

Reference Example 7 m-Heptyloxy-N-(m-hydroxyphenyl)benzamide
Melting point: 115~117° C.

Reference Example 8

-continued

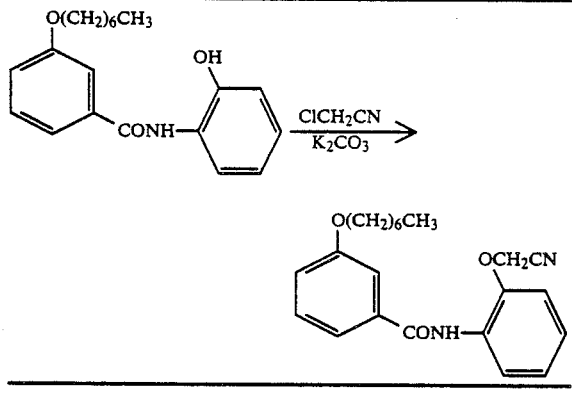

A mixture of 1.6 g of m-heptyloxy-N-(o-hydroxyphenyl)benzamide obtained in Reference Example 5, 0.5 g of chloroacetonitrile, 0.8 g of anhydrous potassium carbonate, 0.1 g of potassium iodide, 0.1 g of tetra-n-butyl ammonium bromide and 20 ml of methyl ethyl ketone was vigorously stirred at 80° C. for 1 hour. After cooling, 100 ml of ethyl acetate was added to the reaction mixture. The mixture was washed with water, dried over anhydrous magnesium sulfate and concentrated under reduced pressure. The residue was recrystallized from ethanol to obtain 1.4 g of m-heptyloxy-N-(o-cyanomethoxyphenyl)benzamide.

Melting point: 105°~106° C.

REFERENCE EXAMPLES 9 TO 11

The following compounds were obtained in a manner similar to Reference Example 8.

Reference Example 9

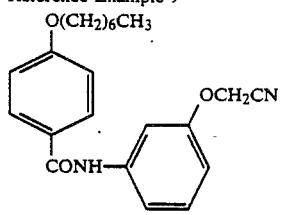

p-Heptyloxy-N-(m-cyanomethoxyphenyl)-benzamide
Melting point: 119~120° C.
Starting Compound: Reference Example 6

Reference Example 10

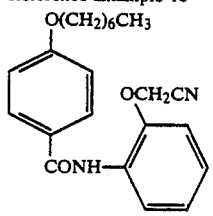

p-Heptyloxy-N-(o-cyanomethoxyphenyl)-benzamide
Melting point: 97~98° C.
Starting Compound: Reference Example 4

Reference Example 11

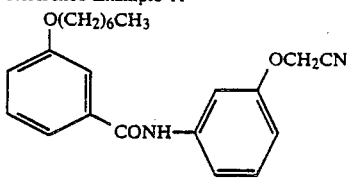

m-Heptyloxy-N-(m-cyanomethoxyphenyl)-benzamide
Melting point: 105~106° C.
Starting Compound: Reference Example 7

Example 1

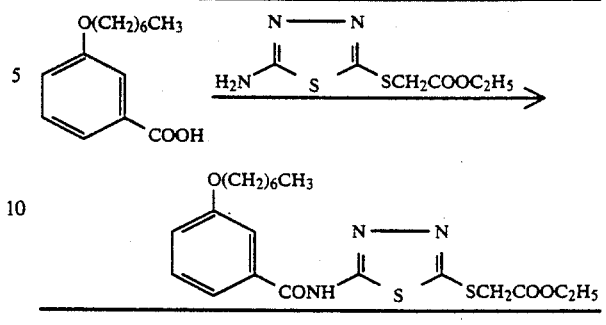

In 10 ml of pyridine were stirred 0.5 g of ethyl [(5-amino-1,3,4-thiadiazol-2-yl)thio]acetate obtained in Reference Example 1, 0.7 g of m-heptyloxybenzoic acid, 0.7 g of dicyclohexylcarbodiimide and 2 to 3 mg of p-toluenesulfonic acid at room temperature for 2 hours. After completion of the reaction, insoluble matters were filtered off and the filtrate was concentrated under reduced pressure. The residue was extracted with ethyl acetate. After washing the extract with water and drying, the solvent was removed by distillation to obtain a solid material. The solid material was washed with a mixture of toluene-n-hexane (2:1) and dried to obtain 1.0 g of ethyl [[5-(m-heptyloxybenzamido)-1,3,4-thiadiazol-2-yl]thio]acetate. Melting point: 114°~116° C.

Elemental analysis for $C_{20}H_{27}N_3O_4S_2$

|  | C % | H % | N % |
| --- | --- | --- | --- |
| Calcd. | 54.90 | 6.22 | 9.60 |
| Found | 55.20 | 6.29 | 9.77 |

In a manner similar to Example 1, Compounds of Examples 7 and 10 described hereafter were obtained.

EXAMPLE 2

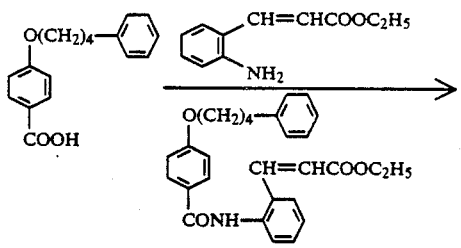

A solution of 0.4 g of ethyl o-aminocinnamate obtained in Reference Example 3 in 4 ml of pyridine was cooled to lower than −20° C. and 0.7 g of p-(4-phenylbutoxy)benzoyl chloride obtained by thionylchlorination of p-(4-phenylbutoxy)benzoic acid in benzene using dimethylformamide as a catalyst was added thereto followed by stirring at room temperature for 30 minutes. To the reaction mixture was added 30 ml of water. The mixture was extracted with ethyl acetate. After washing with water, a 5% aqueous hydrochloric acid solution and water in this order, the extract was dried over anhydrous magnesium sulfate. The solvent was removed by distillation to obtain a solid material. The solid material was dissolved in 10 ml of toluene with heating and 2 ml of n-hexane was added to the solution. After cooling, precipitated crystals were taken by filtration and dried to obtain 0.8 g of ethyl o-[p-(4-phenyl-butoxy)benzamido]cinnamate.

Melting point: 129°~131° C.

Elemental analysis for C$_{28}$H$_{29}$NO$_4$

|  | C % | H % | N % |
|---|---|---|---|
| Calcd. | 75.82 | 6.59 | 3.16 |
| Found | 75.83 | 6.53 | 3.14 |

In a manner similar to Example 2, Compounds of Examples 5, 6 and 8 described hereafter were obtained.

EXAMPLE 3

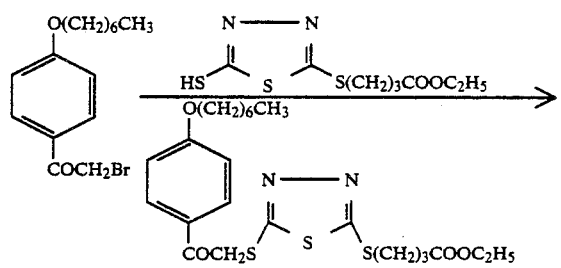

A mixture of 0.6 g of p-heptyloxy-2-bromoacetophenone, 0.6 g of ethyl [5-mercapto-1,3,4-thiadiazol-2-yl)thio]butyrate and 0.4 g of potassium carbonate was heated under reflux for 30 minutes together with 20 ml of acetone. After cooling, insoluble materials were filtered off and the filtrate was concentrated under reduced pressure. The thus obtained solid material was washed with ethanol and dried to obtain 1.0 g of 4-[[5-[(p-heptyloxyphenacyl)thio]-1,3,4-thiadiazol-2-yl]thio]-butyrate. Melting point: 72°~73° C.

Elemental analysis for C$_{23}$H$_{32}$N$_2$O$_4$S$_3$

|  | C % | H % | N % |
|---|---|---|---|
| Calcd. | 55.62 | 6.49 | 5.64 |
| Found | 55.54 | 6.52 | 55.2 |

In a manner similar to Example 3, Compound of Example described hereafter were obtained.

EXAMPLE 4

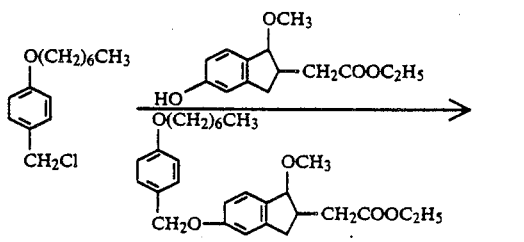

In 2 ml of dimethylformamide were dissolved 190 mg of ethyl 5-hydroxy-1-methoxyindane-2-acetate and 220 mg of p-heptyloxybenzyl chloride. To the solution was added 180 mg of potassium carbonate. The mixture was stirred at 60° C. overnight. After allowing to cool, water and ethyl acetate were added to the mixture. By thoroughly shaking the mixture, the organic layer was separated. After washing with water, drying and concentrating the organic layer, the residue obtained was purified by flash chromatography (eluant: toluene-/ethyl acetate (25/1)) to obtain 220 mg of ethyl 5-(p-heptyloxybenzyloxy)-1-methoxy-2-indaneacetate as a colorless oily product.

Nuclear magnetic resonance spectra (CDCl$_3$, TMS, ppm): 1.89(3H, br), 1.23(3H, t, J=7Hz), 1.2-1.9(10H), 2.3-3.4(5H), 3.41(3H, s), 3.96 (2H, t, J-=7Hz), 4.17 (2H, q, J=7Hz), 4.48 (1H, d, J=3.5Hz), 4.96 (2H, s), 6.8-7.4(7H)

Compounds obtained in Examples 5 to 10 and their physical properties are shown below.

EXAMPLE 5

Desired Compound

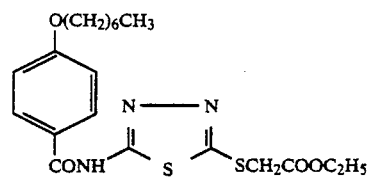

Ethyl[[5-(p-heptyloxybenzamido)-1,3,4-thiadiazol-2-yl]thio]acetate

Physicochemical Properties i) Melting point: 159°~160° C.

ii) Elemental analysis for C$_{20}$H$_{27}$N$_3$O$_4$S$_2$

|  | C % | H % | N % |
|---|---|---|---|
| Calcd. | 54.90 | 6.22 | 9.60 |
| Found | 55.18 | 6.39 | 9.63 |

Starting Compound

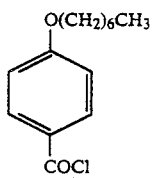 + Compound of Reference Example 1

EXAMPLE 6

Desired Compound

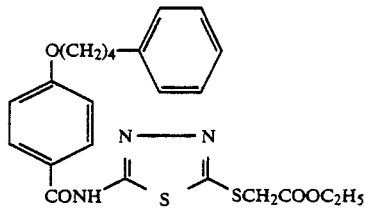

Ethyl[[5-[p-(4-phenylbutoxy)benzamido]-1,3,4-thiadiazol-2-yl]thio]acetate

Physicochemical Properties i) Melting point: 147°~148° C.

ii) Elemental analysis for C$_{23}$H$_{25}$N$_3$O$_4$S$_2$

|  | C % | H % | N % |
|---|---|---|---|
| Calcd. | 58.58 | 5.34 | 8.91 |

-continued

|  | C % | H % | N % |
|---|---|---|---|
| Found | 58.37 | 5.23 | 8.89 |

Starting Compound

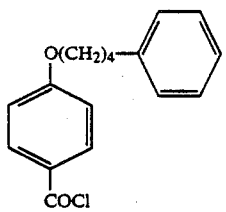

+ Compound of Reference Example 1

EXAMPLE 7

Desired Compound

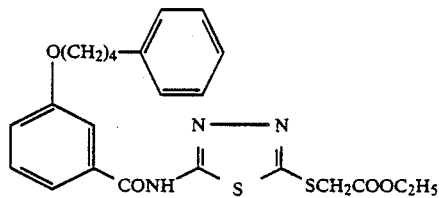

Ethyl[[5-(m-(4-phenylbutoxy)benzamido]-1,3,4-thiadiazol-2-yl]thio]acetate

Physicochemical Properties i) Melting point: 124° ~ 126° C.

ii) Elemental analysis for $C_{23}H_{25}N_3O_4S_2$

|  | C % | H % | N % |
|---|---|---|---|
| Calcd. | 58.58 | 5.34 | 8.91 |
| Found | 58.80 | 5.36 | 8.83 |

Starting Compound

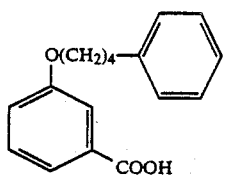

+ Compound of Reference Example 1

EXAMPLE 8

Desired Compound

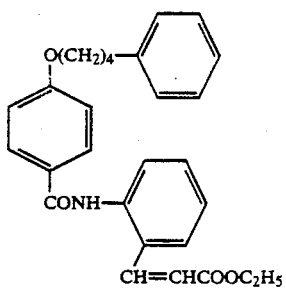

Ethyl o-[p-(4-phenylbutoxy)benzamido]cinnamate.

Physicochemical Properties i) Melting point: 129° ~ 131° C.

ii) Elemental analysis for $C_{28}H_{29}NO_4$

|  | C % | H % | N % |
|---|---|---|---|
| Calcd. | 75.82 | 6.59 | 3.16 |
| Found | 75.83 | 6.53 | 3.14 |

Starting Compound

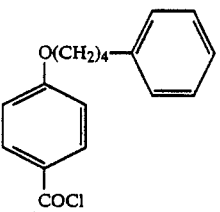

+ Compound of Reference Example 3

EXAMPLE 9

Desired Compound

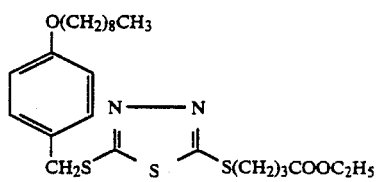

Ethyl 4-[[5-(p-heptyloxybenzyl)thio-1,3,4-thiadiazol-2-yl]thio]butyrate

Physicochemical Properties i) Melting point: 56° ~ 57° C.

ii) Elemental analysis for $C_{22}H_{32}N_2O_3S_3$

|  | C % | H % | N % |
|---|---|---|---|
| Calcd. | 56.38 | 6.88 | 5.98 |
| Found | 56.32 | 7.08 | 5.87 |

Starting Compound

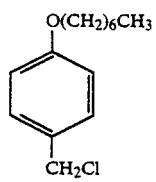

+ Compound of Reference Example 2

EXAMPLE 10

Desired Compound

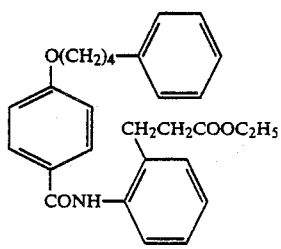

Ethyl 3-[o-[p-(4-phenylbutoxy)benzamido]-phenyl]propionate

Physicochemical Properties i) oily substance ii) Nuclear magnetic resonance spectra (CDCl$_3$, TMS, ppm): 1.10(3H,t), 1.5–2.0(4H), 2.4–3.0(6H), 3.8–4.3(4H), 6.8–8.2(13H)

Starting Compound

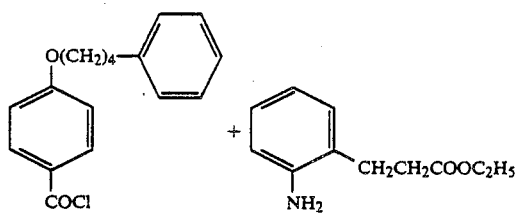

EXAMPLE 11

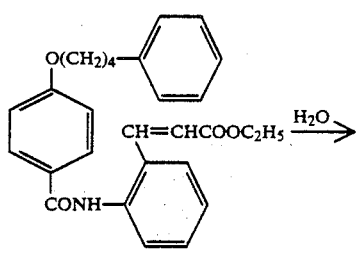

-continued

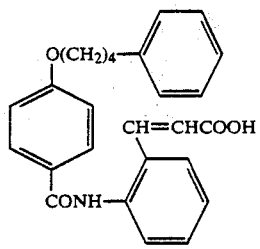

Ethyl o-[p-(4-phenylbutoxy)benzamido]cinnamate, 0.5 g, obtained in Example 2 was heated under reflux for 10 minutes together with 2 ml of 50% potassium hydroxide and 20 ml of methanol. After 20 ml of water was added to the reaction mixture, 10% hydrochloric acid was added to render the system acidic. The precipitated crystals were taken by filtration, washed with water and ethanol and dried to obtain 0.15 g of o-[p-(4-phenylbutoxy)benzamido]cinnamic acid.

Melting point: 129°–131° C. (recrystallized from ethanol).

Elemental analysis for $C_{28}H_{29}NO_4$

|  | C % | H % | N % |
|---|---|---|---|
| Calcd. | 75.82 | 6.59 | 3.16 |
| Found | 75.83 | 6.53 | 3.14 |

In a manner similar to Example 11, Compounds of Examples 12 to 18 described below were obtained.

EXAMPLE 12

Desired Compound

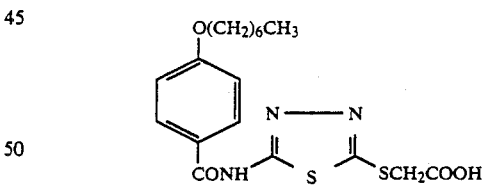

[[5-(p-Heptyloxybenzamido)-1,3,4-thiadiazol-2-yl]thio]acetic acid

Physicochemical Properties i) Melting point: 246°–248° C.

ii) Elemental analysis for $C_{18}H_{23}N_3O_4S_2$

|  | C % | H % | N % |
|---|---|---|---|
| Calcd. | 52.79 | 5.66 | 10.26 |
| Found | 52.93 | 5.75 | 10.19 |

Starting compound: Compound of Example 5

EXAMPLE 13

Desired Compound

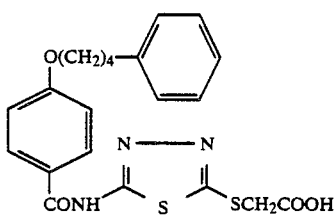

[[5-[p-(4-Phenylbutoxy)benzamido]-1,3,4-thiadiazol-2-yl]thio]acetic acid

Physicochemical Properties i) Melting point: 244°~245° C.
ii) Elemental analysis for $C_{21}H_{21}N_3O_4S_2$

|  | C % | H % | N % | S % |
|---|---|---|---|---|
| Calcd. | 56.87 | 4.77 | 9.47 | 14.46 |
| Found | 56.68 | 4.57 | 9.43 | 14.31 |

Starting compound: Compound of Example 6

EXAMPLE 14

Desired Compound

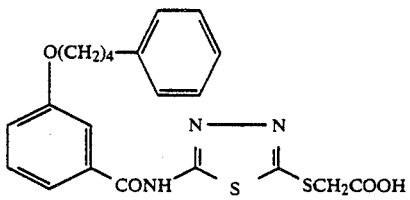

[[5-[m-(4-Phenylbutoxy)benzamido]-1,3,4-thiadiazol-2-yl]thio]acetic acid

Physicochemical Properties i) Melting point: 182°~183° C.
ii) Elemental analysis for $C_{21}H_{21}N_3O_4S_2$

|  | C % | H % | N % | S % |
|---|---|---|---|---|
| Calcd. | 56.87 | 4.77 | 9.47 | 14.46 |
| Found | 56.93 | 4.62 | 9.37 | 14.30 |

Starting compound: Compound of Example 7

EXAMPLE 15

Desired Compound

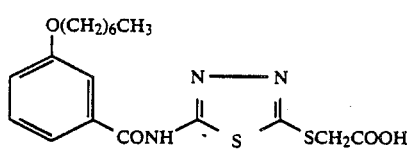

[[5-(m-Heptyloxybenzamido)-1,3,4-thiadiazol-2-yl]thio]acetic acid

Physicochemical Properties i) Melting point: 196°~198° C.
ii) Elemental analysis for $C_{18}H_{23}N_3O_4S_2$

|  | C % | H % | N % |
|---|---|---|---|
| Calcd. | 52.79 | 5.66 | 10.26 |
| Found | 52.78 | 5.58 | 10.14 |

Starting compound: Compound of Example 1

EXAMPLE 16

Desired Compound

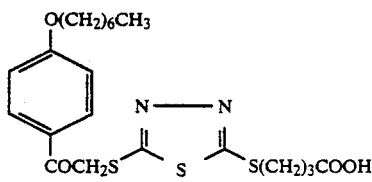

4-[[5-[(p-Heptyloxyphenacyl)thio]-1,3,4-thiadiazol-2-yl]thio]butyric acid

Physicochemical Properties i) Melting point: 116°~117° C.
ii) Elemental analysis for $C_{21}H_{28}N_2O_4S_3$

|  | C % | H % | N % |
|---|---|---|---|
| Calcd. | 53.82 | 6.02 | 5.98 |
| Found | 53.60 | 6.05 | 5.87 |

Starting compound: Compound of Example 3

EXAMPLE 17

Desired Compound

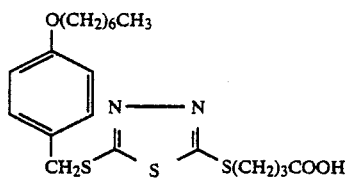

4-[[5-[(p-Heptyloxybenzyl)thio]-1,3,4-thiadiazol-2-yl]thio]butyric acid

Physicochemical Properties i) Melting point: 106°~107° C.
ii) Elemental Analysis for $C_{20}H_{28}N_2O_3S_3$

|  | C % | H % | N % |
|---|---|---|---|
| Calcd. | 54.51 | 6.40 | 6.36 |
| Found | 54.49 | 6.54 | 6.36 |

Starting Compound: Compound of Example 9

EXAMPLE 18

Desired Compound

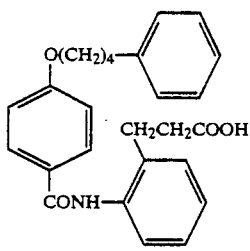

3-[o-[p-(4-Phenylbutoxy)benzamido]phenyl]propionic acid

Physicochemical Properties i) Melting point: 154°~156° C.
ii) Elemental analysis for $C_{26}H_{27}NO_4$

|  | C % | H % | N % |
|---|---|---|---|
| Calcd. | 74.80 | 6.52 | 3.35 |
| Found | 74.48 | 6.87 | 3.63 |

Starting compound: Compound of Example 10

EXAMPLE 19

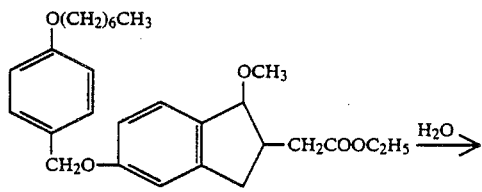

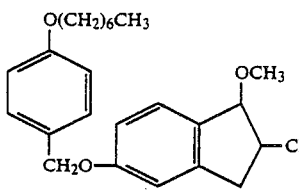

In 1 ml of tetrahydrofuran and 8 ml of methanol were dissolved 220 mg of ethyl 5-(p-heptyloxybenzyloxy)-1-methoxy- 2-indaneacetate obtained in Example 4. After 1 ml of a 5% aqueous sodium hydroxide solution was added to the solution, the mixture was stirred at room temperature for 8 hours. After diluting with water, the system was rendered acidic with hydrochloric acid followed by extraction with ethyl acetate. The ethyl acetate layer was washed with water, dried and concentrated. The obtained crystalline residue was recrystallized from ether-pentane to obtain 150 mg of 5-(p-heptyloxybenzyloxy)-1-methoxy-2-indaneacetic acid.

Melting point: 80°~82° C.
Elemental analysis for $C_{26}H_{34}O_5$

|  | C % | H % |
|---|---|---|
| Calcd. | 73.21 | 8.03 |
| Found | 73.20 | 8.26 |

EXAMPLE 20

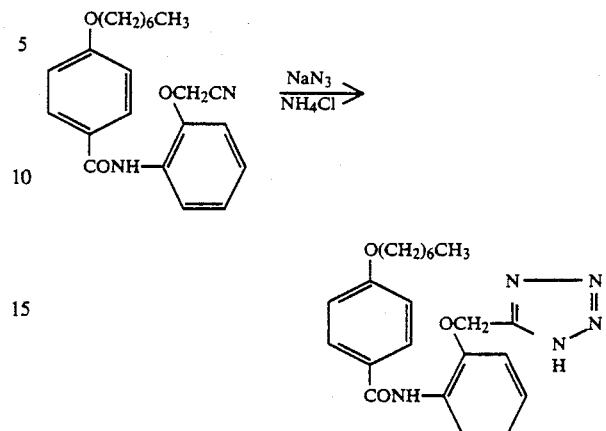

A mixture of 500 mg of p-heptyloxy-N-(o-cyanomethoxyphenyl)benzamide obtained in Reference Example 10, 116 mg of sodium azide, 95 mg of ammonium chloride and 10 ml of dimethylformamide was stirred at 140° to 150° C. overnight. After cooling, 50 ml of water was added to the reaction mixture followed by washing with ethyl acetate. The aqueous layer was rendered acidic with diluted hydrochloric acid and extracted with ethyl acetate. The extract was washed with water, dried over anhydrous magnesium sulfate and concentrated under reduced pressure. The residue was recrystallized from ethanol to obtain 300 mg of 4-heptyloxy-2'-(5-tetrazolylmethoxy)benzanilide.

Melting point: 148°~150° C.
Elemental analysis for $C_{22}H_{27}N_5O_3$

|  | C % | H % | N % |
|---|---|---|---|
| Calcd. | 64.53 | 6.65 | 17.10 |
| Found | 64.65 | 6.70 | 17.13 |

In a manner similar to Example 20, Compounds of Examples 21 to 23 described hereafter were obtained.

EXAMPLE 21

Desired Compound

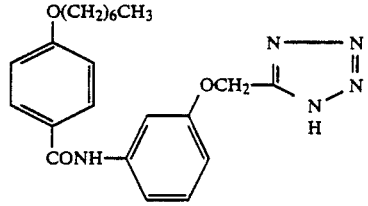

4-Heptyloxy-3'-(5-tetrazolylmethoxy)benzanilide

Physicochemical Properties i) Melting point: 187°~190° C.
ii) Elemental Analysis for $C_{22}H_{27}N_5O_3$

|  | C % | H % |
|---|---|---|
| Calcd. | 64.53 | 6.65 |

-continued

| | C % | H % |
|---|---|---|
| Found | 64.64 | 6.81 |

Starting Compound: Compound of Reference Example 9

EXAMPLE 22

Desired Compound

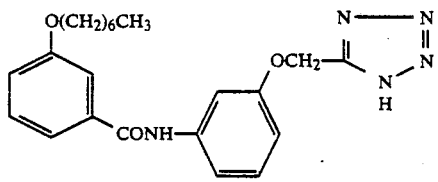

3-Heptyloxy-3'-(5-tetrazolylmethoxy)benzanilide

Physicochemical Properties i) Melting point: 149°~150° C.
ii) Elemental analysis for $C_{22}N_{27}N_5O_3$

| | C % | H % | N % |
|---|---|---|---|
| Calcd. | 64.53 | 6.65 | 17.10 |
| Found | 64.55 | 6.77 | 17.02 |

Starting compound: Compound of Reference Example 11

EXAMPLE 23

Desired Compound

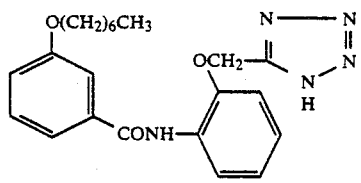

3-Heptyloxy-2'-(5-tetrazolylmethoxy)benzanilide

Physicochemical Properties i) Melting point: 108°~110° C.
ii) Elemental analysis for $C_{22}H_{27}N_5O_3$

| | C % | H % | N % |
|---|---|---|---|
| Calcd. | 64.53 | 6.65 | 17.10 |
| Found | 64.59 | 6.77 | 17.13 |

Starting compound: Compound of Reference Example 8

REFERENCE EXAMPLE 12

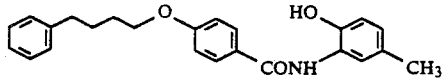

One drop of N,N-dimethylformamide was added to a solution of 1 g of p-(4-phenylbutoxy)benzoic acid in 5 ml of methylene chloride and 2 ml of oxalyl chloride was added to the mixture at −30° C. or lower. The mixture was stirred at room temperature for 3 hours. The reaction mixture was concentrated under reduced pressure to obtain crude p-(4-phenylbutoxy)benzoyl chloride. This substance was dissolved in 5 ml of methylene chloride and the resulting solution was added to a solution of 1 g of 2-amino-4-methylphenol in 5 ml of pyridine under ice cooling followed by stirring at room temperature for 3 hours. The reaction mixture was poured into conc. hydrochloric acid-ice and then extracted with ethyl acetate. The extract was washed subsequently with water, an aqueous solution of sodium hydrogen carbonate and again water. After drying over anhydrous magnesium sulfate, the system was concentrated under reduced pressure to obtain 1.4 g of 2'-hydroxy-5'-methyl-4-(4-phenylbutoxy)benzanilide.
Melting point: 138°~140° C.

REFERENCE EXAMPLE 13

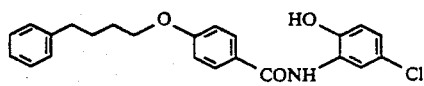

In a manner similar to Reference Example 12 except for using 1 g of 2-amino-4-chlorophenol as a starting material, 1.42 g of 5'-chloro-2'-hydroxy-4-(4-phenylbutoxy)benzanilide was obtained.
Melting point: 137°~139° C.

REFERENCE EXAMPLE 14

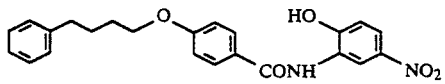

In a manner similar to Reference Example 12 except for using 400 mg of 2-amino-4-nitrophenol as a starting material, 450 mg of 2'-hydroxy-5'-nitro-4-(4-phenylbutoxy)benzanilide was obtained.
Melting point: 174°~176° C.

REFERENCE EXAMPLE 15

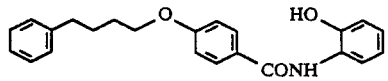

In a manner similar to Reference Example 12 except for using 400 mg of 2-aminophenol as a starting material, 630 mg of 2'-hydroxy-4-(4-phenylbutoxy)benzanilide was obtained.
Melting point: 116°~117° C.

REFERENCE EXAMPLE 16

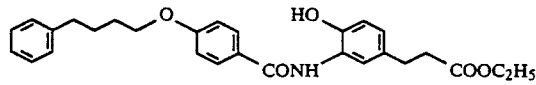

In a manner similar to Reference Example 12 except for using 1 g of ethyl 3-(3-amino-4-hydroxyphenyl)propionate hydrochloride as a starting material, 1.6 g of ethyl 3-[4-hydroxy-3-[p-(4-phenylbutoxy)benzoyl]amidophenyl]propionate was obtained.
Melting point: 94°~96° C.

REFERENCE EXAMPLE 17

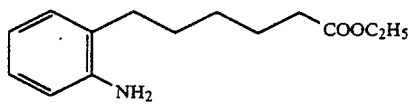

A mixture Of 1.6 g of sodium hydroxide (60%, oil) in 60 ml of dimethylsulfoxide was stirred at 55°~60° C. for 1 hour. After lowering to room temperature, a solution of 9 g of (4-carboxybutyl)triphenyl phosphonium bromide in 20 ml of dimethylsulfoxide was added to the mixture. After stirring at room temperature for 30 minutes, a solution of 3 g of o-nitrobenzaldehyde in 10 ml of dimethylsulfoxide was added thereto. The mixture was stirred at room temperature for 2 hours. The reaction mixture was poured into cold diluted hydrochloric acid followed by extraction with ether. After washing with water, the extract was dried over anhydrous magnesium sulfate and concentrated under reduced pressure to obtain oily 6-(o-nitrophenyl)-5-hexenic acid. This substance was added to a mixture of 20 ml of ethanol and 4 ml of conc. surfuric acid. The resulting mixture was heated under reflux for 3 hours. The reaction mixture was concentrated under reduced pressure and water was added to the residue followed by extracting with toluene. The extract was washed with water, a diluted aqueous sodium hydrogen carbonate and water, in order. After drying over anhydrous magnesium sulfate, the system was concentrated under reduced pressure. The residue was applied to silica gel column chromatography and eluted with toluene to obtain 0.73 g of ethyl 6-(o-nitrophenyl)-5-hexenate.

This substance was dissolved in 10 ml of ethanol and 0.1 g of 10% palladium-carbon was added to the solution. Catalytic reduction was performed until absorption of hydrogen was discontinued. The catalyst was filtered off and the filtrate was concentrated under reduced pressure to obtain 0.6 g of ethyl 6-(o-aminophenyl)hexanate.

Nuclear magnetic resonance spectra (CDCl₃, TMS internal standard, ppm): 1.24(t, 3H), 1.0–2.0(m, 6H), 2.30(t, 2H), 2.49(t,2H), 2.8–3.8(2H), 4.10(q, 2H), 6.5–7.2(m,4H)

REFERENCE EXAMPLE 18

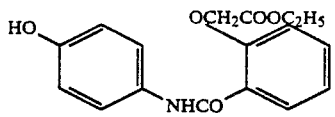

In a manner similar to Reference Example 12 except for using 2 g of o-ethoxycarbonylmethoxybenzoic acid and 1 g of 2-aminophenol as starting materials, 1.5 g of ethyl o-[(p-hydroxyphenyl)carbamoyl]phenoxyacetate was obtained. Melting point: 208°~210° C.

REFERENCE EXAMPLE 19

A mixture of 2.0 g of ethyl mercaptoacetate, 3.13 g of 1-bromo-3-chloropropane, 2.29 g of anhyrous potassium carbonate and 10 ml of dimethylformamide was stirred at room temperature for 3 hours. The reaction mixture was diluted with toluene and insoluble matters were filtered off. The filtrate was washed with an aqueous sodium hydroxide and water in order, dried over anhydrous magnesium sulfate and concentrated under reduced pressure. The residue was applied to silica gel column chromatography and eluted with a mixture of hexane-ethyl acetate (15:1) to obtain 2.65 g of oily ethyl [(3-chloropropyl)thio]acetate.

Nuclear magnetic resonance spectra (CDCl₃, TMS internal standard, ppm): 1.28(t, 3H), 1.9–2.2(2H), 2.7–2.9(2H), 3.20(s, 3H), 3.64(t, 2H), 4.19(q, 2H)

Mass spectrum m/z: 196(M⁺)

REFERENCE EXAMPLE 20

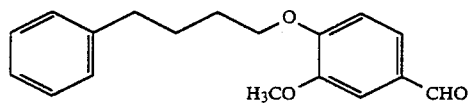

A mixture of 860 mg of vaniline, 1.00 g of 4-bromobutylbenzene, 1.00 g of potassium carbonate and 8 ml of 2-butanone was heated under reflux for 3 hours. The reaction mixture was poured into water and the product was extracted with ether. The ethereal layer was washed with water, dried and concentrated. The obtained residue was applied to silica gel column chromatography and eluted with toluene to obtain 500 mg of 4-(4-phenylbutoxy)-3-methoxybenzaldehyde.

Nuclear magnetic resonance spectra (CDCl₃, TMS internal standard, ppm): 1.8–2.0(4H), 2.71(t, 2H, J=7Hz), 3.89(s, 3H), 4.08(t,2H, J=7Hz), 6.92(d, 1H, J=9.5Hz), 7.15–7 50(7H), 9.85(s, 1H)

REFERENCE EXAMPLE 21

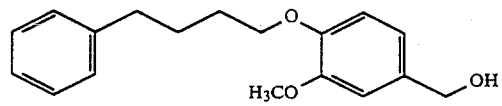

In 5 ml of methanol was dissolved 660 mg of 4-(4-phenylbutoxy)-3-methoxybenzamide obtained in Reference Example 20 and, 200 mg of sodium borohydride was gradually added to the solution at 0° C. After stirring for 1 hour, water and ethyl acetate were added to the mixture followed by vigorously stirring. The ethyl acetate layer obtained by separation was washed subsequently with water and an aqueous saline solution and then concentrated. The residue was applied to silica gel column chromatography and eluted with toluene:ethyl acetate (10:1) to obtain 430 mg of 4-(4-phenylbutoxy)-3-methoxybenzyl alcohol.

Nuclear magnetic resonance spectra (CDCl₃, TMS internal standard, ppm): 1.7–1.9(4H), 2.68(t, 2H, J=7Hz), 3.87(s, 3H), 4.00(t, 2H, J=7Hz), 4.60(d, 1H, J=5.5Hz, s, after addition of D₂O), 6.8–6.95 (3H), 7.15–7.3

REFERENCE EXAMPLE 22

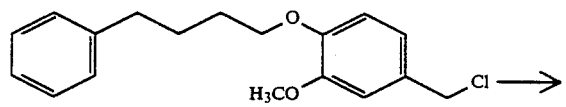

-continued

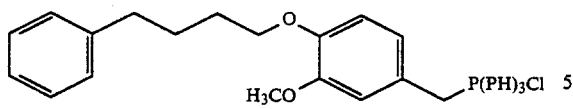

To a solution of 410 mg of 4-(4-phenylbutoxy)-3-methoxybenzyl alcohol obtained in Reference Example 21 in 0.5 ml of toluene and 2 ml of benzene was added 0.5 ml of thionyl chloride at 0° C. The mixture was stirred for 20 minutes and a saturated sodium bicarbonate aqueous solution was added thereto. The reaction mixture was separated. After washing with water and a saline aqueous solution, the organic layer was concentrated. The residue was applied to silica gel column chromatography and eluted with toluene:heaxane:ethyl acetate (20:15:1) to obtain 300 mg of 4-chloromethyl-2-methoxy-1-(4-phenylbutoxy)benzene.

Nuclear magnetic resonance spectra (CDCl$_3$, TMS internal standard, ppm): 1.75~1.95(4H),2.68(t,2H,J=7Hz),3.87(s,3H),4.01(d,2-H, J=7Hz),4.52(s,2H),6.80~6.90(3H),7.15~7.25(5H)

The product described above was dissolved in 2 ml of xylene and the solution was treated together with 304 mg of triphenyl phosphine at a reflux temperature for 1.5 hours. After cooling, the precipitated colorless crystals were collected by suction and dried under reduced pressure to obtain 260 mg of [4-(4-phenylbutoxy)-2-methoxybenzyl]triphenylphosphonium chloride.

Melting point: 119°~128° C.
Mass spectrum m/z: 531 (M+-Cl)

REFERENCE EXAMPLE 23

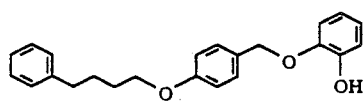

In a manner similar to Reference Examples 20 to 22 except for using salicylaldehyde as a starting material, o-(4-phenylbutoxy)benzyltriphenylphosphonium chloride was obtained.

Melting point: 214°~216° C.

REFERENCE EXAMPLE 24

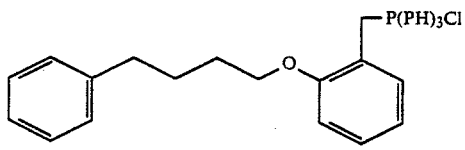

In 1.5 ml of N,N-dimethylformamide were stirred 390 mg of 4-chloromethyl-1-(4-phenylbutoxy)benzene, 180 mg of catechol and 270 mg of potassium carbonate at room temperature overnight. The reaction mixture was dispersed in water and ethyl acetate and the dispersion was separated. The ethyl acetate layer washed subsequently with water and an aqueous saline solution, dried and concentrated. The obtained residue was applied to silica gel column chromatography and eluted with toluene to obtain 240 mg of o-[p-(4-phenylbutoxy)benzyloxy]phenol.

Nuclear magnetic resonance spectra (CDCl$_3$, TMS internal standard, ppm): 1.7–2.0(4H), 2.5–2.8(2H), 3.8–4.1(2H), 4.95(s, 2H), 5.63 (s, 1H, vanishing after addition of D$_2$O)

REFERENCE EXAMPLE 25

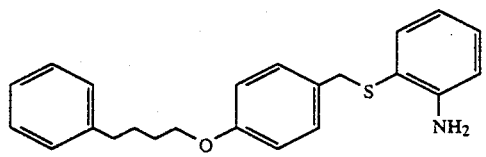

o-[[p-(4-Phenylbutoxy)benzyl]thio]aniline was obtained from 4-chloromethyl-1-(4-phenylbutoxy)benzene and o-aminothiophenol in a manner similar to Reference Example 24.

Nuclear magnetic resonance spectra (CDCl$_3$, TMS internal standard, ppm): 1.7–1.9(4H), 2.6–2.8(2H), 3.85(s, 2H), 3.8–4.0(2H), 4.2(broad, 2H, vanishing after addition of D$_2$O), 6.5–7.3 (13H)

EXAMPLE 24

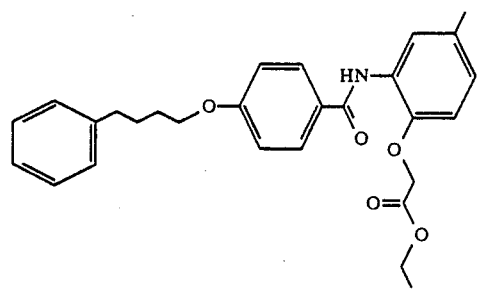

A mixture of 1.3 g of 2'-hydroxy-5'-methyl-4-(4-phenylbutoxy)benzanilide obtained in Reference Example 12, 0.64 g of ethyl bromoacetate, 0.48 g of anhydrous potassium carbonate, 20 ml of 2-butanone and a catalytic amount of tetra-n-butylammonium bromide was heated under reflux for 3 hours. To the reaction mixture was added 100 ml of toluene. After washing with a diluted sodium hydroxide aqueous solution and water in this order, the system was dried over anhydrous magnesium sulfate and concentrated under reduced pressure and then recrystallized from isopropyl alcohol to obtain 1.5 g of ethyl 4-methyl-2-[p-(4-phenylbutoxy)benzamido]phenoxyacetate.

Physicochemical Properties

1) Melting point: 79°~80° C.
2) Elemental analysis for C$_{28}$H$_{31}$NO$_5$

|  | C % | H % | N % |
|---|---|---|---|
| Calcd. | 72.86 | 6.77 | 3.03 |
| Found | 72.80 | 6.68 | 2.87 |

Compounds of Examples 25 through 32 were obtained in a manner similar to Example 24.

EXAMPLE 25

Ethyl 4-chloro-2-[p-(4-phenylbutoxy)benzamido]phenoxyacetate

Physicochemical Properties

1) Melting point: 81°~84° C.
2) Elemental analysis for $C_{27}H_{28}ClNO_5$

|  | C % | H % | N % | Cl % |
|---|---|---|---|---|
| Calcd. | 67.28 | 5.86 | 2.91 | 7.36 |
| Found | 67.33 | 5.87 | 2.82 | 7.31 |

Starting Compound

Compound of Reference Example 13 + $BrCH_2COOC_2H_5$

EXAMPLE 26

Ethyl 4-nitro-2-[p-(4-phenylbutoxy)benzamido]phenoxyacetate

Physicochemical Properties

1) Melting point: 113° C.
2) Elemental analysis for $C_{27}H_{28}N_2O_7$

|  | N % |
|---|---|
| Calcd. | 5.09 |
| Found | 5.39 |

Starting Compound

Compound of Reference Example 14 + $BrCH_2COOC_2H_5$

EXAMPLE 27

Ethyl o-[p-(4-phenylbutoxy)benzamido]phenoxyacetate

Physicochemical Properties

1) Oily product
2) Elemental analysis for $C_{27}H_{29}NO_5$

|  | C % | H % | N % |
|---|---|---|---|
| Calcd. | 72.46 | 6.53 | 3.13 |
| Found | 72.22 | 6.53 | 3.05 |

Starting Compound

Compound of Reference Example 15 + $BrCH_2COOC_2H_5$

EXAMPLE 28

Ethyl 3-[4-ethoxycarbonylmethoxy-3-[p-(4-phenylbutoxy)benzamido]phenyl]propionate

Physicochemical Properties

1) Melting point: 61°~62° C.
2) Elemental analysis for $C_{32}H_{37}NO_7$

|  | C % | H % | N % |
|---|---|---|---|
| Calcd. | 70.18 | 6.81 | 2.56 |
| Found | 70.13 | 6.73 | 2.47 |

Starting Compound

Compound of Reference Example 16 + $BrCH_2COOC_2H_5$

EXAMPLE 29

Ethyl [[3-[4-chloro-2-[p-(4-phenylbutoxy)-benzamido]phenoxy]propyl]thio]acetate

Physicochemical Properties

1) Melting point: 70°~73° C.

2) Elemental analysis for $C_{30}H_{34}NO_5SCl$

|  | N % |
|---|---|
| Calcd. | 2.52 |
| Found | 2.71 |

Starting Compound

Compound of Reference Example 13 + Compound of Reference Example 19

EXAMPLE 30

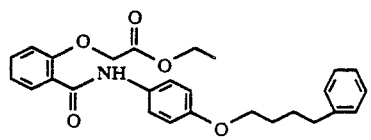

Ethyl o-[N-[p-(4-phenylbutoxy)phenyl]carbamoyl]phenoxy]acetate

Physicochemical Properties

1) Melting point: 86°~88° C.
2) Elemental analysis for $C_{27}H_{29}NO_5$

|  | C % | H % | N % |
|---|---|---|---|
| Calcd. | 72.46 | 6.53 | 3.13 |
| Found | 72.54 | 6.62 | 3.10 |

Starting Compound

Compound of Reference Example 18 + Br(CH$_2$)$_4$Ph

EXAMPLE 31

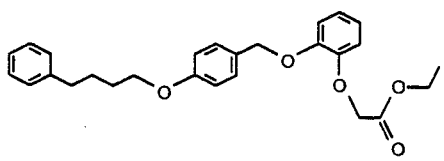

Ethyl o-[p-(4-phenylbutoxy)benzyloxy]phenoxyacetate

Physicochemical Properties

1) Oily product
2) Nuclear magnetic resonance spectra: (CDCl$_3$, TMS internal standard, ppm)
1.24(t,3H),1.6~1.8(4H),2.5~2.7(2),3.8~4.0(6H),4.16 (q,2H),4.61(s,2H),5.02(s,2H),6.7~7.3(13H)

Starting Compound

Compound of Reference Example 24 + BrCH$_2$COOC$_2$H$_5$

EXAMPLE 32

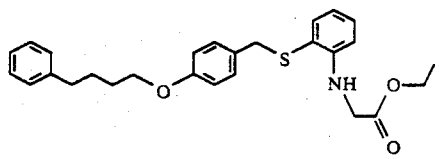

Ethyl N-[o-[[p-(4-phenylbutoxy)benzyl]thio]phenyl]glycine

Physicochemical Properties

1) Oily product
2) Nuclear magnetic resonance spectra: (CDCl$_3$, TMS internal standard, ppm)
1.28(t,3H),1.7~1.9(4H),2.6~2.8(2H),3.8~4.0(6H),4.27 (q,2H),5.64(1H),6.6~7.3(13H)

Starting Compound

Compound of Reference Example 25 + BrCH$_2$COOC$_2$H$_5$

EXAMPLE 33

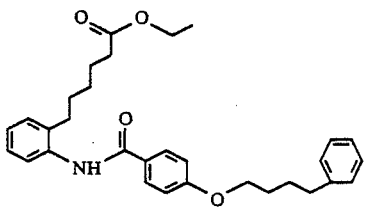

A solution of p-(4-phenylbutoxy)benzoyl chloride prepared from 1 g of p-(phenylbutoxy)benzoic acid and 2 ml of oxalyl chloride in methylene chloride was added to a solution of 0.6 g of ethyl 6-(o-aminophenyl)hexanate obtained in Reference Example 17 in 10 ml of pyridine at temperature less than −30° C. The mixture was stirred at room temperature overnight and concentrated under reduced pressure. Toluene was added to the residue. The mixture was washed with diluted hydrochloric acid and then with water and dried over anhydrous magnesium sulfate. The systems was concentrated under reduced pressure to obtain 1.0 g of oily ethyl 6-[o-[p-(4-phenylbutoxy)benzamido]phenyl]hexanate.

Physicochemical Properties

1) Melting point: Oily product
2) Nuclear magnetic resonance spectra: (CDCl$_3$, TMS internal standard, ppm)
1.20(t,3H),1.0~2.0(m,10H),2.26(t,2H),2.4~2.8(m,4H), 4.0(t,2H),4.08(q,2H),6.8~8.2(m,13H)
3) Mass spectrum m/z: 487 (M+)

EXAMPLE 34

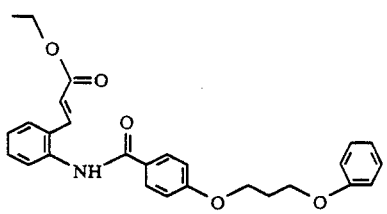

Ethyl o-[p(3-phenoxypropoxy)benazmido]cinnamate, 0.52 g, was obtained in a manner similar to Example 31 except that (3-phenoxypropoxy)benzoyl chloride prepared from 0.5 g of (3-phenoxypropoxy)benzoic acid and 1 ml of oxalyl chloride and 0.3 g of ethyl o-aminocinnamate were used as starting compounds.

Physicochemical Properties

1) Melting point: 155°~157° C.
2) Elemental analysis for $C_{27}H_{27}NO_5$

|  | C % | H % | N % |
|---|---|---|---|
| Calcd. | 72.79 | 6.11 | 3.14 |
| Found | 72.69 | 6.10 | 3.15 |

EXAMPLE 35

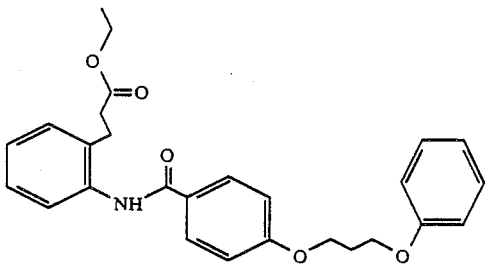

To a solution of 250 mg of ethyl o-[p-(3-phenoxypropoxy)benzamido]cinnamate obtained in Example 34 in 10 ml of methanol and 20 ml of ethyl acetate was added 10% palladium-carbon. Catalytic reduction was performed until absorption of hydrogen was discontinued. The catalyst was filtered off and the residue was recrystallized from isopropyl alcohol to obtain 200 mg of ethyl 3-[o-[p-(3-phenoxypropoxy)benzamido]-phenyl]propionate.

Physicochemical Properties

1) Melting point: 89°~90° C.
2) Elemental analysis for $C_{27}H_{29}NO_5$

|  | C % | H % | N % |
|---|---|---|---|
| Calcd. | 72.46 | 6.53 | 3.13 |
| Found | 72.27 | 6.54 | 3.12 |

EXAMPLE 36

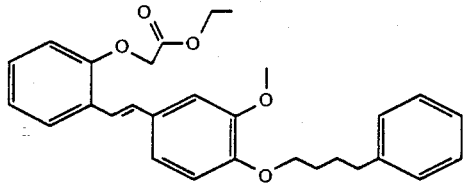

To a suspension of 260 mg of [4-(4-phenylbutoxy)-2-methoxybenzyl]triphenylphosphonium choride obtained in Reference Example 22 in 2.5 ml of tetrahydrofuran was dropwise added 0.36 ml of a 1.42M n-butyl lithium/hexane solution. The mixture was stirred for 10 minutes to form a dark red solution. The solution was dropwise added to a solution of 114 mg of ethyl o-formylphenoxyacetate in 1 ml of tetrahydrofuran at 0° C. using an injection tube. After stirring for 20 minutes, a saturated ammonium chloride aqueous solution was added thereto. The product was extracted with ether. After washing with water and then an aqueous saline solution, the ethereal layer was dried and concentrated. The crude product was fractionated and separated by TLC (developer; hexane:methylene chloride:acetone=8:2:1) to obtain 170 mg of ethyl o-[3-methoxy-4-(4-phenylbutoxy)styryl]phenoxyacetate.

Physicochemical Properties

1) Nuclear magnetic resonance spectra: (CDCl₃, TMS internal standard, ppm) 1.27, 1.29( each of them is t, 3H by joining, J=7.2Hz), 1.75–1.9(4H), 2.6–2.75(2H), 3.52(s, 3H), 3.95–4.40 (4H), 4.61, 4.66 (each of them is s, 2H by joining) 6.6–7.6 (14H)

EXAMPLE 37

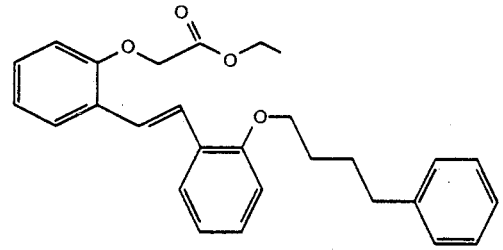

To a suspension of 230 mg of o-(4-phenylbutoxy)benzyltriphenylphosphonium chloride obtained in Reference Example 23 in 2 ml of tetrahydrofuran was dropwise added a 1.4M n-butyl lithiun/hexane solution at 0° C. After stirring for 20 minutes, this deep scarlet solution was dropwise added to a solution of 100 mg of ethyl o-formylphenoxyacetate in 1 ml of tetrahydrofuran at 0° C. After stirring for 50 minutes, a saturated ammonium chloride aqueous solution was added and the product was extracted with ethyl acetate. After washing with water twice and then with a saturated saline aqueous solution, the ethyl acetate layer was dried and concentrated under reduced pressure. The obtained residue, 380 mg, was purified by silica gel fractionation thin layer chromatography to obtain 180 mg of o-[o-(4-phenylbutoxy)styryl]phenoxyacetate as a colorless oily substance.

Physicochemical Properties

1) Oily product
2) Nuclear magnetic resonance spectra (CDCl₃, TMS internal standard, ppm) 1.2–1.4(3H), 1.7–1.9(4H), 2.6–2.8(2H), 3.9–4.4(4H), 4.61 and 4.63(each of them is s, 2H by joining), 6.6–7.7(15H)

EXAMPLE 38

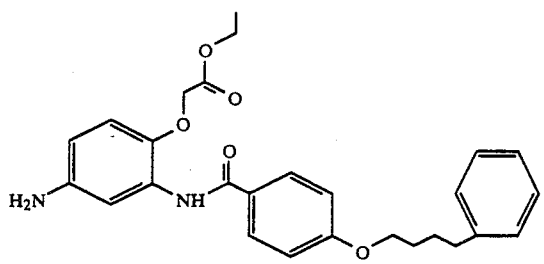

To a mixture of 2.81 g of ethyl 4-nitro-2-[p-(4-phenylbutoxy)benzamido]phenoxyacetate obtained in Example 26 in 50 ml of ethanol-tetrahydrofuran (1:1) was added 0.5 g of 10% palladium-carbon. Catalytic reduction was performed at room temperature under normal pressure until absorption of hydrogen was discontinued. The catalyst was filtered off and the filtrate was concentrated under reduced pressure. The obtained crystals were washed with isopropyl alcohol to obtain 1.72 g of ethyl 4-amino-2-[p-(4-phenylbutoxy)benzamido]phenoxyacetate.

Physicochemical Properties

1) Melting point: 88°~90° C.
2) Nuclear magnetic resonance spectra: (CDCl₃, TMS internal standard, ppm) 1.26(t,3H), 1.5–2.0(m, 4H), 2.4–2.8(m, 2H), 3.8–4.2 (m, 2H), 4.22(q, 2H), 4.60(s, 2H), 6.0–7.0(m, 12H)

EXAMPLE 39

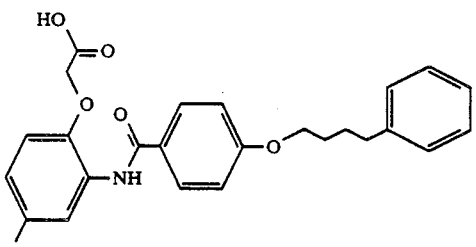

To 20 ml of a 10% potassium hydroxide-90% methanol solution was added 1.5 g of ethyl 4-methyl-2-[p-(4-phenylbutoxy)benzamido]phenoxyacetate obtained in Example 24 followed by stirring at 50° to 60° C. for 1 hour. After adding 10 ml of a saturated saline aqueous solution, the reaction mixture was rendered acidic with diluted hydrochloric acid followed by extraction with ethyl acetate. The extract was washed with water, dried over anhydrous magnesium sulfate and concentrated under reduced pressure. The residue was recrystallized from ethyl acetate to obtain 1.12 g of 4-methyl-2-[p-(4-phenylbutoxy)benzamido]phenoxyacetic acid.

Physicochemical Properties

1) Melting point: 122°~123° C.

2) Elemental analysis for C₂₆H₂₇NO₅

|  | C % | H % | N % |
|---|---|---|---|
| Calcd. | 72.04 | 6.28 | 3.23 |
| Found | 71.79 | 6.23 | 3.20 |

Compounds of Examples 40 through 52 were prepared in a manner similar to Example 39.

EXAMPLE 40

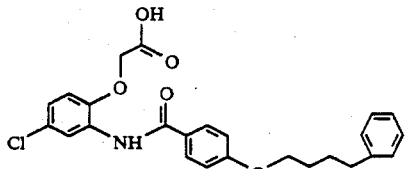

4-Chloro-2-[p-(4-phenylbutoxy)benzamido]phenoxyacetic acid

Physicochemical Properties

Melting point: 139°~140° C.
Elemental analysis for C₂₅H₂₄NO₅Cl

|  | C % | H % | N %. |
|---|---|---|---|
| Calcd. | 66.15 | 5.33 | 3.09 |
| Found | 66.01 | 5.34 | 3.16 |

Starting compound: Compound of Example 25

EXAMPLE 41

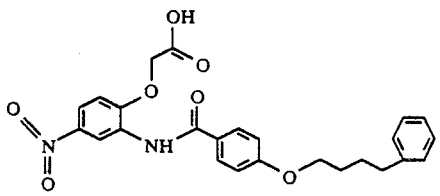

4-Nitro-2-[p-(4-phenylbutoxy)benzamido]phenoxyacetic acid

Physicochemical Properties

1) Melting point: 168°~170° C.
2) Elemental analysis for C₂₅H₂₄N₂O₇

|  | C % | H % | N % |
|---|---|---|---|
| Calcd. | 64.65 | 5.21 | 6.03 |
| Found | 64.47 | 5.29 | 5.89 |

Starting compound: Compound of Example 26

EXAMPLE 42

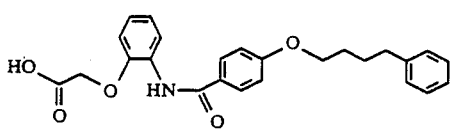

o-[p-(4-Phenylbutoxy)benzamido]phenoxyacetic acid

Physicochemical Properties

1) Melting point: 135°~137° C.
2) Elemental analysis for $C_{25}H_{25}NO_5$

|  | C % | H % | N % |
|---|---|---|---|
| Calcd. | 71.58 | 6.01 | 3.34 |
| Found | 71.54 | 5.98 | 3.35 |

Starting compound: Compound of Example 27

EXAMPLE 43

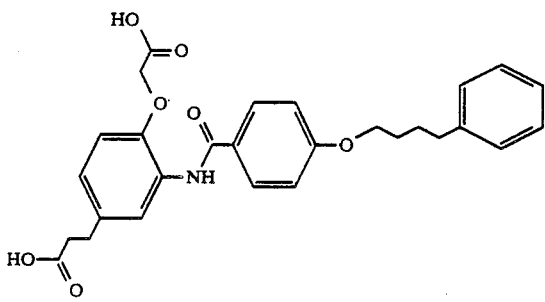

3-[4-Carbomethoxy-3-[p-(4-phenyl-butoxy)benzamido]phenyl]-propionic acid

Physicochemical Properties

1) Melting point: 218°~220° C.
2) Elemental analysis for $C_{28}H_{29}NO_7$

|  | C % | H % | N % |
|---|---|---|---|
| Calcd. | 68.42 | 5.95 | 2.85 |
| Found | 68.27 | 6.00 | 2.90 |

Starting compound: Compound of Example 28

EXAMPLE 44

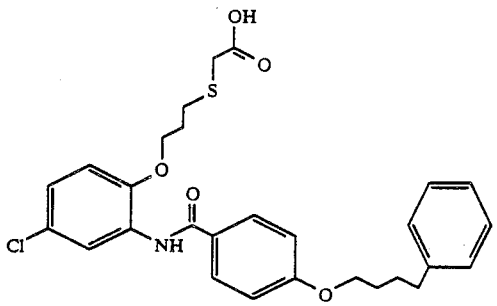

[[3-[4-Chloro-2-]p-(4-phenyl-butoxy)benzamido]phenoxy]propyl]-thio]acetic acid

Physicochemical Properties

1) Melting point: 94°~96° C.
2) Elemental analysis for $C_{28}H_{30}NO_5SCl$

|  | C % | H % | N % |
|---|---|---|---|
| Calcd. | 63.69 | 5.73 | 2.65 |
| Found | 63.54 | 5.78 | 2.56 |

Starting compound: Compound of Example 29

EXAMPLE 45

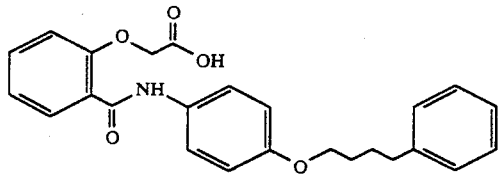

o-[N-[p-(4-Phenylbutoxy)phenyl]car-bamoyl]phenoxyacetic acid

Physicochemical Properties

1) Melting point: 150°~152° C.
2) Elemental analysis for $C_{25}H_{25}NO_5$

|  | C % | H % | N % |
|---|---|---|---|
| Calcd. | 71.58 | 6.01 | 3.34 |
| Found | 71.41 | 6.12 | 3.43 |

Starting compound: Compound of Example 30

EXAMPLE 46

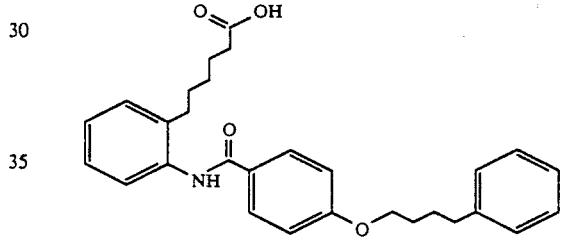

6-[o-[p-(4-Phenylbutoxy)benzamido]phenyl]hexanic acid

Physicochemical Properties

1) Melting point: 125°~127° C.
2) Elemental analysis for $C_{29}H_{33}NO_4$

|  | C % | H % | N % |
|---|---|---|---|
| Calcd. | 75.79 | 7.24 | 3.05 |
| Found | 75.61 | 7.27 | 3.01 |

Starting compound: Compound of Example 33

EXAMPLE 47

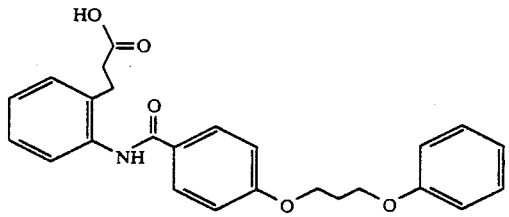

3-[o-[p-(3-Phenoxypropoxy)benzamido]phenyl]propionic acid

Physicochemical Properties

1) Melting point: 161°~163° C.

2) Elemental analysis for $C_{25}H_{25}NO_5$

|  | C % | H % | N % |
|---|---|---|---|
| Calcd. | 71.58 | 6.01 | 3.34 |
| Found | 71.49 | 6.05 | 3.50 |

Starting compound: Compound of Example 35

EXAMPLE 48

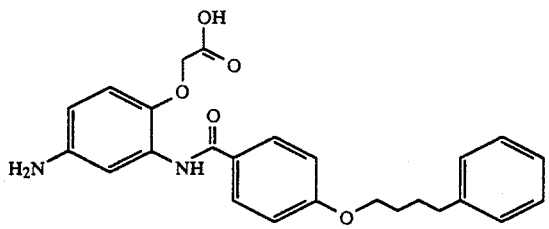

4-Amino-2-[p-(4-phenylbutoxy)benzamido]phenoxyacetic acid

Physicochemical Properties

1) Melting point: 178°~180° C.
2) Elemental analysis for $C_{25}H_{26}N_2O_5$

|  | N % |
|---|---|
| Calcd. | 6.45 |
| Found | 6.32 |

Starting compound: Compound of Example 38

EXAMPLE 49

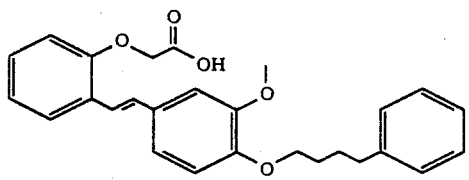

o-[p-(4-Phenylbutoxy)benzyloxy]phenoxyacetic acid

Physicochemical Properties

1) Oily product
2) Elemental analysis for $C_{25}H_{26}O_5$

|  | C % | H % |
|---|---|---|
| Calcd. | 73.78 | 6.45 |
| Found | 73.65 | 6.47 |

Starting compound: Compound of Example 31

EXAMPLE 50

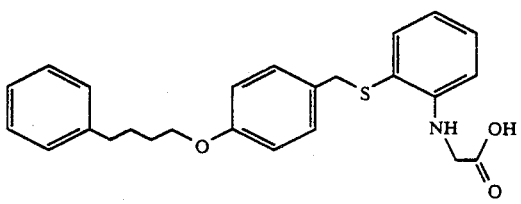

N-[o-[[p-(4-Phenylbutoxy)benzyl]thio]phenyl]glycine

Physicochemical Properties

1) Melting point: 135°~137° C.
2) Elemental analysis for $C_{25}H_{27}NO_3S$

|  | C % | H % | N % | S % |
|---|---|---|---|---|
| Calcd. | 71.23 | 6.46 | 3.32 | 7.61 |
| Found | 71.01 | 6.43 | 3.32 | 7.73 |

Starting compound: Compound of Example 32

EXAMPLE 51

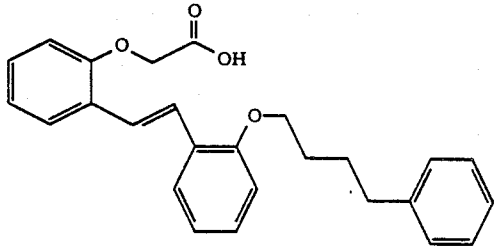

o-[3-Methoxy-4-(4-phenylbutoxy)styryl]phenoxyacetic acid was obtained from Compound of Example 36 except that the product was purified by silica gel column chromatography (eluate=chloroform:methanol (12:1)) in lieu of recrystallization.

Physicochemical Properties

1) Oily product
2) Nuclear magnetic resonance spectra: (CDCl$_3$, TMS internal standard, ppm) 1.7-1.9(4H), 2.6-2.8(2H), 3.63(s, 3H), 3.9-4.1(2H), 4.60, 4.74(each of them is s, 2H by joining), 5.35 (broad, vanishing after addition of D$_2$O)

EXAMPLE 52 o-[o-(4-phenylbutoxy)styryl]phenoxyacetic acid

Physicochemical Properties

1) Oily product
2) Nuclear magnetic resonance spectra: (CDCl$_3$, TMS internal standard, ppm) 1.7-2.0(4H), 2.6-2.8(2H), 3.9–4.1(2H), 4.54 and 4.69 (each of them is s, 2H by joining), 6.1(broad, vanishing after addition of D₂O), 6.6–7.7

Starting compound: Compound of Example 37

REFERENCE EXAMPLE 26

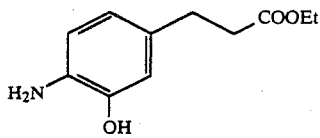

In 30 ml of tetrahydrofuran and 130 ml of ethanol was dissolved 3.32 g of ethyl 3-hydroxy-4-nitrocinnamate. To the solution was added 100 mg of 10% palladium-carbon. The mixture was stirred under normal pressure in a hydrogen flow until absorption of hydrogen was discontinued. The catalyst was filtered off by suction and the filtrate was concentrated under reduced pressure to obtain 3.10 g of crude ethyl 4-amino-3-hydroxybenzenepropionate as an oily substance.

Nuclear magnetic resonance spectra: (CDCl₃, TMS internal standard, ppm): 1.22(3H, t), 2.4–2.8(2H), 3.5–3.8(2H), 4.10(2H, q), 6.60(3H).

REFERENCE EXAMPLE 27

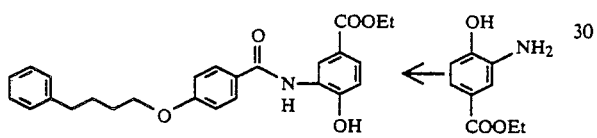

One drop of N,N-dimethylformamide was added to a solution of 1.41 g of p-(4-phenylbutoxy)benzoic acid in 35 ml of methylene chloride and 1.5 ml of oxalyl chloride was further added to the mixture under ice cooling. The mixture was stirred for 30 minutes and at room temperature for an additional 1 hour. The reaction mixture was concentrated under reduced pressure to obtain crude p-(4-phenylbutoxy)benzoyl chloride. This acid chloride was dissolved in 15 ml of methylene chloride and the resulting solution was added to a solution of 0.93 g of ethyl 3-amino-4-hydroxybenzoate in 8 ml of pyridine and 10 ml of methylene chloride under ice cooling. The mixture was stirred for 1.5 hours. The reaction mixture was poured into 10% hydrochloric acid at 0° C. and the product was extracted with ethyl acetate. After washing with a saturated sodium hydrogen carbonate solution, water and then a saturated saline aqueous solution in this order, the ethyl acetate layer was dried over anhydrous magnesium sulfate and concentrated under reduced pressure. The obtained crystalline residue was recrystallized from hexane-ethyl acetate to obtain 1.47 g of ethyl 3-hydroxy-4-[p-(4-phenylbutoxy)benzamido]benzoate.

Melting point: 156°–158° C.
Elemental analysis for C₂₆H₂₇NO₅

|  | C % | H % | N % |
|---|---|---|---|
| Calcd. | 72.04 | 6.28 | 3.24 |
| Found | 71.79 | 6.26 | 3.16 |

Compounds of Reference Examples 28 through 36 were produced in a similar manner.

REFERENCE EXAMPLE 28

Desired Compound

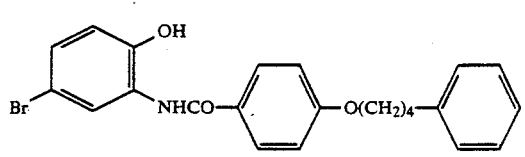

Physicochemical Properties i) Melting point: 145°–147° C.
ii) Elemental analysis for C₂₃H₂₂BrNO₃

|  | C % | H % | N % | Br % |
|---|---|---|---|---|
| Calcd. | 62.74 | 5.04 | 3.18 | 18.15 |
| Found | 62.57 | 5.01 | 3.05 | 18.21 |

Starting Compound

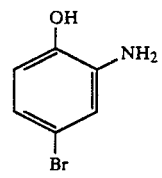

+

(phenylbutoxybenzoyl chloride structure)

REFERENCE EXAMPLE 29

Desired Compound

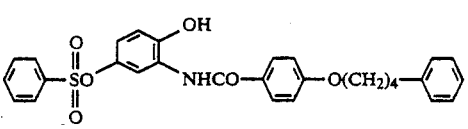

2'-Hydroxy-4-(4-phenylbutoxy)-5'-phenylsulfonyloxybenzanilide

Physicochemical Properties i) Melting point: 169°–171° C.
ii) Elemental analysis for C₂₉H₂₇NO₆S

|  | C % | H % | N % | S % |
|---|---|---|---|---|
| Calcd. | 67.29 | 5.26 | 2.71 | 6.20 |
| Found | 67.08 | 5.32 | 2.59 | 6.26 |

Starting Compound

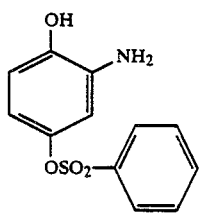

+

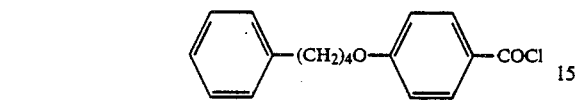

REFERENCE EXAMPLE 30
Desired Compound

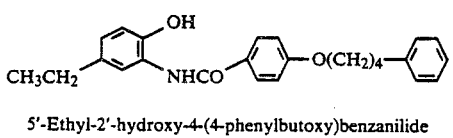

5'-Ethyl-2'-hydroxy-4-(4-phenylbutoxy)benzanilide

Physicochemical Properties i) Melting point: 122°–124° C.
ii) Elemental analysis for $C_{25}H_{27}NO_3$

|  | C % | H % | N % |
|---|---|---|---|
| Calcd. | 77.09 | 6.99 | 3.60 |
| Found | 77.00 | 7.14 | 3.62 |

Starting Compound

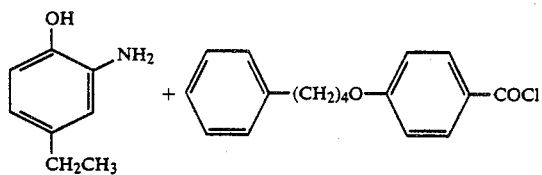

REFERENCE EXAMPLE 31
Desired Compound

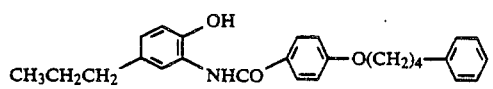

2'-Hydroxy-4-(4-phenylbutoxy)-5'-propylbenzanilide

Physicochemical Properties i) Melting point: 125°–128° C.
ii) Elemental analysis for $C_{26}H_{29}NO_3$

|  | C % | H % | N % |
|---|---|---|---|
| Calcd. | 77.39 | 7.24 | 3.47 |
| Found | 77.55 | 7.24 | 3.44 |

Starting Compound

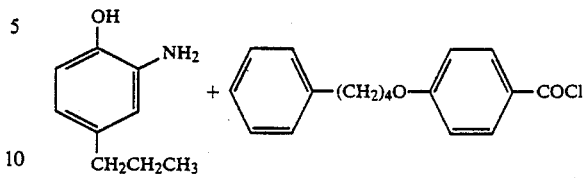

REFERENCE EXAMPLE 32
Desired Compound

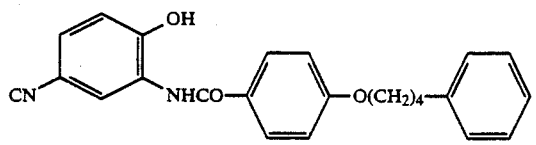

5'-Cyano-2'-hydroxy-4-(4-phenylbutoxy)benzanilide

Physicochemical Properties i) Melting point: 153°–154° C.
ii) Elemental analysis for $C_{24}H_{22}N_2O_3$

|  | C % | H % | N % |
|---|---|---|---|
| Calcd. | 74.59 | 5.73 | 7.25 |
| Found | 74.69 | 5.79 | 7.21 |

Starting Compound

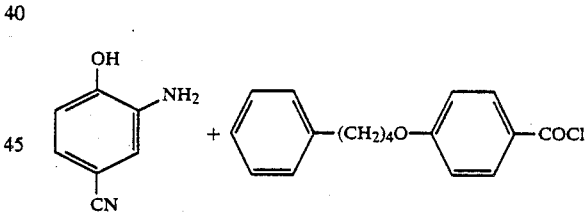

REFERENCE EXAMPLE 33
Desired Compound

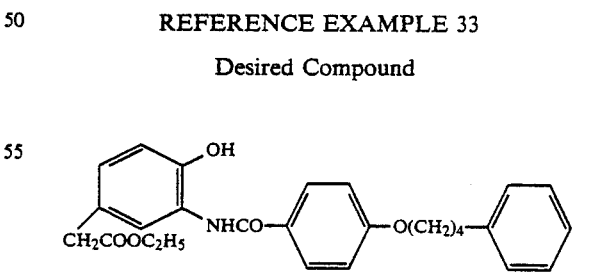

Ethyl 4-hydroxy-3-[p-(4-phenylbutoxy)benzamido]phenylacetate i) Oily product
ii) Nuclear magnetic resonance spectra: (CDCl$_3$, internal standard: TMS, ppm) 1.23(3H, t), 1.7–2.0(4H), 2.6–2.8(2H), 3.45(2H, s), 3.9–4.2(2H), 4.08(2H, q), 6.8–8.2(12H)

Starting Compound

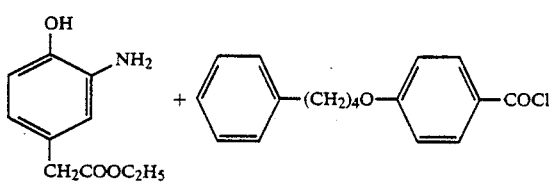

REFERENCE EXAMPLE 34

Desired Compound

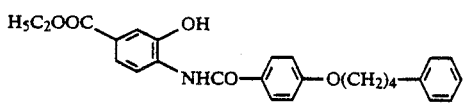

Ethyl 3-hydroxy-4-[p-(4-phenylbutoxy)benzamido]-benzoate

Physicochemical Properties i) Melting point: 148°–149° C.
ii) Elemental analysis for $C_{26}H_{27}NO_5$

|  | C % | H % | N % |
|---|---|---|---|
| Calcd. | 72.04 | 6.28 | 3.23 |
| Found | 71.81 | 6.37 | 3.60 |

Starting Compound

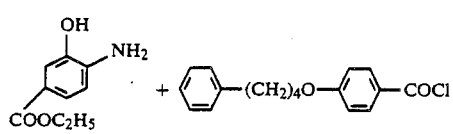

REFERENCE EXAMPLE 35

Desired Compound

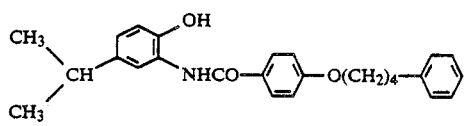

2′-Hydroxy-5′-isopropyl-4-(4-phenylbutoxy)benzanilide

Physicochemical Properties i) Melting point: 105°–107° C.
ii) Elemental analysis for $C_{26}H_{29}NO_3$

|  | C % | H % | N % |
|---|---|---|---|
| Calcd. | 77.39 | 7.24 | 3.47 |
| Found | 77.47 | 7.23 | 3.35 |

Starting Compound

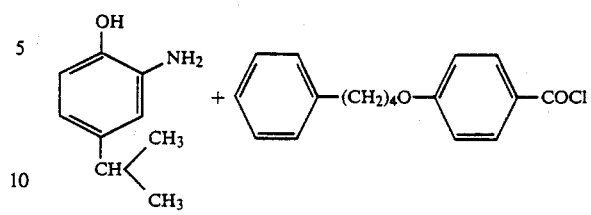

REFERENCE EXAMPLE 36

Desired Compound

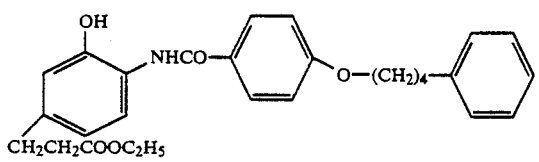

Ethyl 3-[3-hydroxy-4-[p-(4-phenylbutoxy)benzamido]-phenyl] propionate

Physicochemical Properties i) Melting point: 105°–107° C.
ii) Elemental analysis for $C_{28}H_{31}NO_5$

|  | C % | H % | N % |
|---|---|---|---|
| Calcd. | 72.86 | 6.77 | 3.03 |
| Found | 72.71 | 6.81 | 2.91 |

Starting Compound: Reference Example 26+

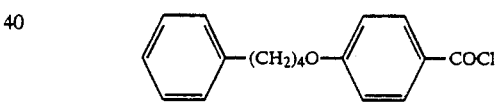

REFERENCE EXAMPLE 37

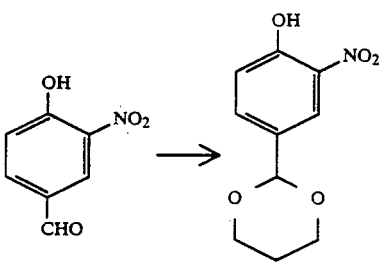

A mixture of 8 g of 4-hydroxy-3-nitrobenzaldehyde, 16 g of 1,3-propanediol, a catalytic amount of pyridinium p-toluenesulfonic acid and 250 ml of toluene was azeotropically dehydrated with heating under reflux. The reaction mixture was cooled, washed with water, dried over anhydrous magnesium sulfate and then concentrated under reduced pressure. The residue was recrystallized from toluene-n-hexane to obtain 9.2 g of 4-(1,3-dioxan-2-yl)-2-nitrophenol.

Melting point: 70°–71° C.

REFERENCE EXAMPLE 38

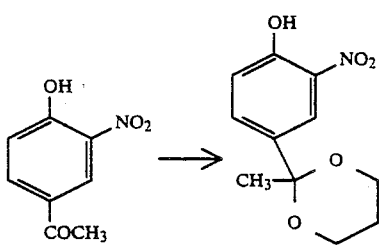

In a manner similar to Reference Example 37, 2.8 g of 4-(1-methyl-1,3-dioxan-2-yl)-2-nitrophenol was obtained using 3 g of 4'-hydroxy-3'-nitroacetophenone as a starting compound.

Melting point: 109°-111° C.

REFERENCE EXAMPLE 39

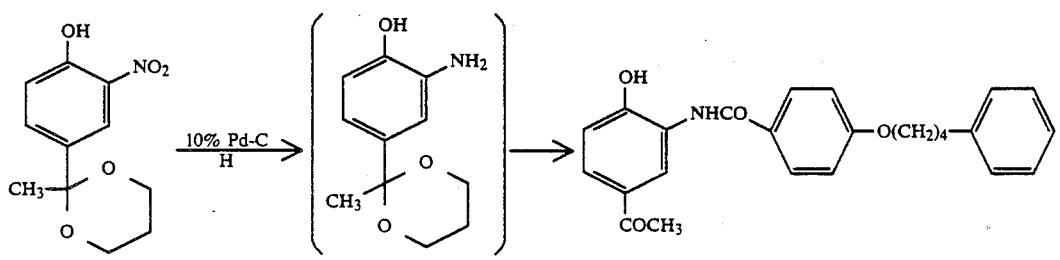

A solution of 4 g of 4-(1,3-dioxan-2-yl)-2-nitrophenol obtained in Reference Example 37 was catalytically reduced at room temperature until absorption of hydrogen was discontinued. The catalyst was filtered off and 5 ml of pyridine was added to the mother liquor. The mixture was cooled to temperatures lower than −20° C. To the mixture was added p-(4-phenylbutoxy)benzoyl chloride prepared from 4.8 g of p-(4-phenylbutoxy)benzoic acid in a manner similar to Reference Example 27. The mixture was stirred at room temperature for 2 hours and 200 ml of ethyl acetate was added thereto. After washing with diluted hydrochloric acid, water, a diluted sodium hydrogen carbonate aqueous solution and then water in this order, the system was dried over anhydrous magnesium sulfate and concentrated under reduced pressure to obtain 7.5 g of 5'-(1,3-dioxan-2-yl)-2'-hydroxy(4-phenylbutoxy)benzanilide.

Melting point: 122°-123° C.

Elemental analysis for $C_{27}H_{29}NO_5$

|  | C % | H % | N % |
|---|---|---|---|
| Calcd. | 72.46 | 6.53 | 3.13 |
| Found | 72.50 | 6.60 | 3.06 |

REFERENCE EXAMPLE 40

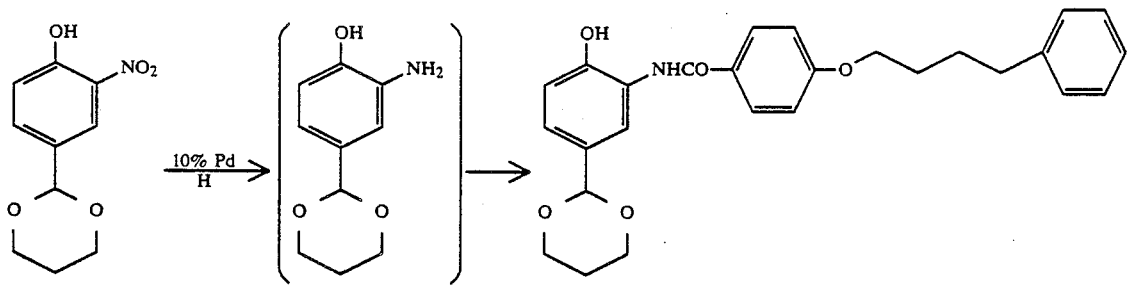

In a manner similar to Reference Example 39, 2.5 g of 5'-acetyl-2'-hydroxy-(4-phenylbutoxy)benzanilide was obtained except that 1.5 g of 4-(1-methyl-1,3-dioxan-2-yl)-2-nitrophenol obtained in Reference Example 38 was used as a starting compound.

Melting point: 134°-135° C.

Elemental analysis for $C_{25}H_{25}NO_4$

|  | C % | H % | N % |
|---|---|---|---|
| Calcd. | 74.42 | 6.25 | 3.47 |
| Found | 74.20 | 6.27 | 3.43 |

REFERENCE EXAMPLE 41

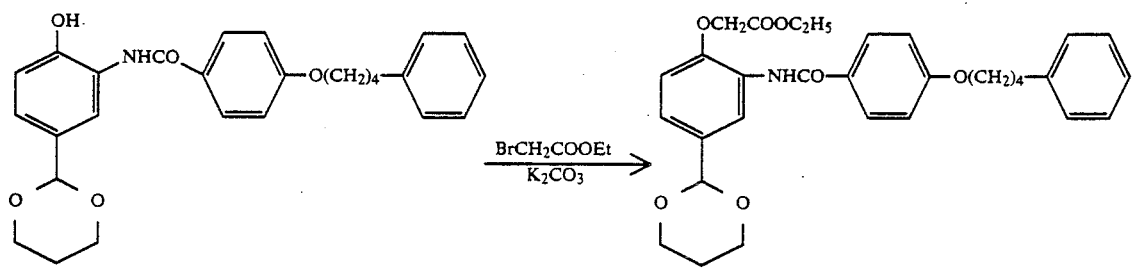

A mixture of 7.5 g of 5'-(1,3-dioxan-2-yl)-2'-hydroxy-(4-phenylbutoxy)benzanilide obtained in Reference Example 39, 2.97 g of ethyl bromoacetate, 2.7 g of anhydrous potassium carbonate, a catalytic amount of tetra-n-butylammonium bromide and 100 ml of 2-butanone was stirred at 60° to 65° C. for 6 hours. To the reaction mixture was added 300 ml of toluene. The system was washed with a diluted sodium hydroxide aqueous solution and then with water, dried over anhydrous magnesium sulfate and concentrated under reduced pressure to obtain 8.69 g of ethyl 4-(1,3-dioxan-2-yl)-2-[p-(4-phenylbutoxy)benzamido]phenoxyacetate.

Melting point: 73° C.

Elemental analysis for $C_{31}H_{35}NO_7$

|  | C % | H % | N % |
|---|---|---|---|
| Calcd. | 69.78 | 6.61 | 2.62 |
| Found | 69.68 | 6.58 | 2.49 |

REFERENCE EXAMPLE 42

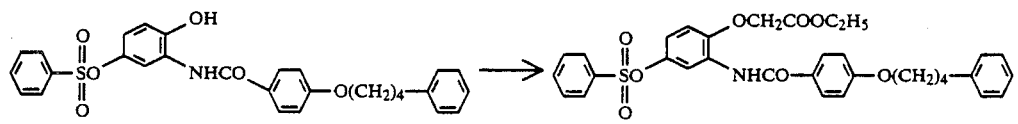

In a manner similar to Reference Example 41, 0.91 g of ethyl 2-[p-(4-phenylbutoxy)benzamido]-4-phenylsulfonyloxy phenoxyacetate was obtained except that 0.80 g of 2'-hydroxy-4-(4-phenylbutoxy)-5'-phenylsulfonyloxybenzanilide obtained in Reference Example 39 was used as a starting compound.

Melting point: 85°–87° C.

Elemental analysis for $C_{33}H_{33}NO_8S$

|  | C % | H % | N % | S % |
|---|---|---|---|---|
| Calcd. | 65.66 | 5.51 | 2.32 | 5.31 |
| Found | 65.45 | 5.45 | 2.23 | 5.48 |

REFERENCE EXAMPLE 43

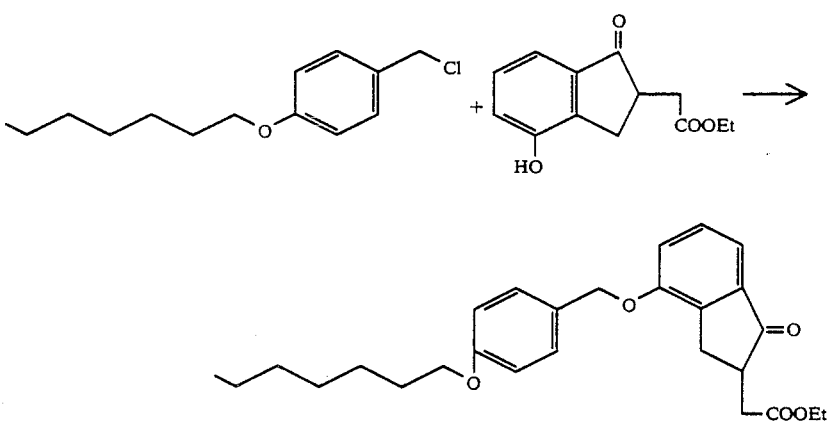

In 15 ml of 2-butanone were heated under reflux 2.27 g of ethyl 4-hydroxyindan-1-one-2-acetate, 2.10 g of p-heptyloxybenzyl chloride and 2.00 g of potassium carbonate overnight. Water was added to the reaction mixture and the product was extracted with ethyl acetate. The ethyl acetate layer was washed with water and then with a saturated saline aqueous solution and dried over anhydrous magnesium sulfate. Volatile matters were removed under reduced pressure and the obtained residue was purified by silica gel column chromatography (eluant: toluene-ethyl acetate (20:1)) to obtain 2.17 g of ethyl 4-(p-heptyloxybenzyloxy)indan-1-one-2-acetate.

i) Oily product ii) Nuclear magnetic resonance spectra: (CDCl$_3$, internal standard: TMS, ppm) 0.8–0.95(3H), 1.21(3H, t), 1.2–1.4(8H), 1.7–1.9(2H), 2.3–3.1(4H), 3.44(1H, dd), 3.96(2H, t) 4.14(2H, q), 5.08(2H, s), 6.93(2H, d), 7.0–7.4 (5H).

REFERENCE EXAMPLE 44

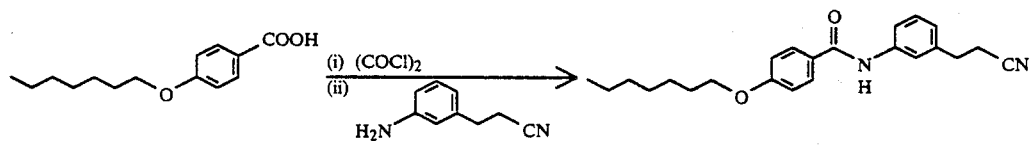

To a solution of 730 mg of p-heptyloxybenzoic acid in 5 ml of methylene chloride were added 10 μl of N,N-dimethylformamide and 410 μl of oxalyl chloride. The mixture was stirred for 1 hour. The reaction mixture was concentrated under reduced pressure to obtain crude p-heptyloxybenzoyl chloride. A solution of p-heptyloxybenzoyl chloride described above in 2 ml of methylene chloride was dropwise added to a solution of 380 mg of 3-(m-aminophenyl)propionitrile in 1.5 ml of pyridine and 4 ml of methylene chloride at −30° C. The mixture was gradually warmed to room temperature and stirred for 3 hours. Water was added and the product was extracted with ethyl acetate. After washing with 5% hydrochloric acid, a saturated sodium hydrogen carbonate aqueous solution, water and then a saturated saline aqueous solution in this order, the ethyl acetate layer was dried over anhydrous magnesium sulfate and concentrated under reduced pressure. The residue was purified by silica gel column chromatography (eluant: toluene-ethyl acetate (10:1)) to obtain 830 mg of 3-[m-[(p-heptyloxy)benzamido]phenyl]propionitrile.

i) Melting point: 129°–131° C.

ii) Nuclear magnetic resonance spectra: (CDCl$_3$, internal standard: TMS, ppm) 0.8–1.0(3H), 1.3–1.6(8H), 1.7–1.9(2H), 2.55–2.75 (2H), 2.90–3.10(2H), 4.03(2H, t), 6.9–7.9(8H).

EXAMPLE 53

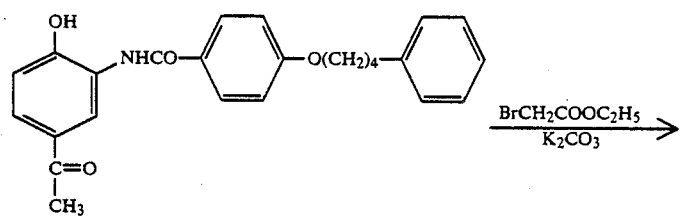

A mixture of 2.5 g of 5'-acetyl-2'-hydroxy-4-(4-phenylbutoxy)benzanilide obtained in Reference Example 40, 1.3 g of ethyl bromoacetate, 1.2 g of anhydrous potassium carbonate, a catalytic amount of tetra-n-butylammonium bromide and 30 ml of 2-butanone was stirred at 60° to 70° C. for 6 hours. To the reaction mixture was added 50 ml of toluene. The mixture was washed with a diluted sodium hydroxide aqueous solution and then with water, dried over anhydrous magnesium sulfate and concentrated under reduced pressure. The residue was recrystallized from isopropyl alcohol to obtain 2.4 g of ethyl 4-acetyl-2-[p-(4-phenylbutoxy)-benzamido]phenoxyacetate.

Melting point: 105°–107° C.

Elemental analysis for C$_{29}$H$_{31}$NO$_6$

|  | C % | H % | N % |
|---|---|---|---|
| Calcd. | 71.15 | 6.38 | 2.86 |
| Found | 70.92 | 6.39 | 2.77 |

Compounds of Examples 54 through 63 were obtained in a similar manner.

EXAMPLE 54

Desired Compound

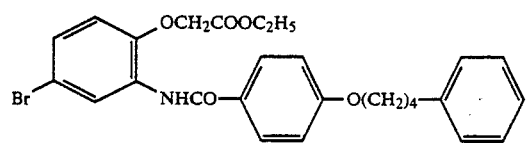

Ethyl 4-bromo-2-[p-(4-phenylbutoxy)benzamido]phenoxyacetate

Physicochemical Properties i) Melting point: 85°–86° C.

ii) Elemental analysis for C$_{27}$H$_{28}$NO$_5$Br

|  | C % | H % | N % | Br % |
|---|---|---|---|---|
| Calcd. | 61.60 | 5.36 | 2.66 | 15.18 |
| Found | 61.58 | 5.35 | 2.61 | 15.20 |

Starting compound: Compound of Reference Example 28 + BrCH$_2$COOC$_2$H$_5$

EXAMPLE 55

Desired Compound

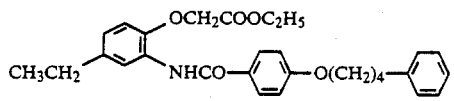

Ethyl 4-ethyl-2-[p-(4-phenylbutoxy)benzamido]phenoxyacetate

Physicochemical Properties i) Melting point: 58°-59° C.
ii) Elemental analysis for $C_{29}H_{33}NO_5$

|  | C % | H % | N % |
|---|---|---|---|
| Calcd. | 73.24 | 6.99 | 2.95 |
| Found | 73.14 | 6.85 | 2.69 |

Starting compound: Compound of Reference Example 30 + $BrCH_2COOC_2H_5$

EXAMPLE 56

Desired Compound

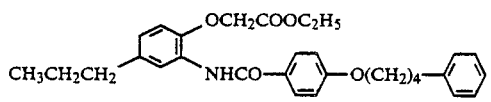

Ethyl 2-[p-(4-phenylbutoxy)benzamido]-4-propylphenoxyacetate

Physicochemical Properties i) Melting point: 57°-58° C.
ii) Elemental analysis for $C_{30}H_{35}NO_5$

|  | C % | H % | N % |
|---|---|---|---|
| Calcd. | 73.60 | 7.21 | 2.86 |
| Found | 73.47 | 7.39 | 2.84 |

Starting compound: Compound of Reference Example 31 + $BrCH_2COOC_2H_5$

EXAMPLE 57

Desired Compound

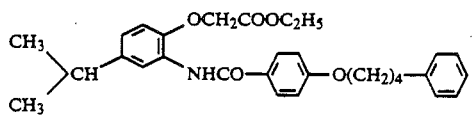

Ethyl 4-isopropyl-2-[p-(4-phenylbutoxy)benzamido]phenoxyacetate

Physicochemical Properties i) Oily product
ii) Elemental analysis for $C_{30}H_{35}NO_5$

|  | C % | H % | N % |
|---|---|---|---|
| Calcd. | 73.60 | 7.21 | 2.86 |
| Found | 73.64 | 7.31 | 2.82 |

Starting compound: Compound of Reference Example 35 + $BrCH_2COOC_2H_5$

EXAMPLE 58

Desired Compound

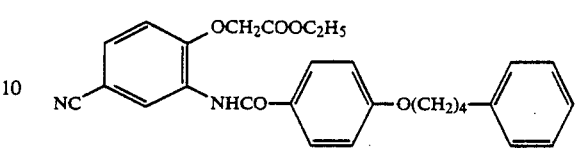

Ethyl 4-cyano-2-[p-(4-phenylbutoxy)benzamido]phenoxyacetate

Physicochemical Properties i) Melting point: 115°-116° C.
ii) Elemental analysis for $C_{28}H_{28}N_2O_5$

|  | C % | H % | N % |
|---|---|---|---|
| Calcd. | 71.17 | 5.97 | 5.93 |
| Found | 71.15 | 6.01 | 5.85 |

Starting compound: Compound of Reference Example 32 + $BrCH_2COOC_2H_5$

EXAMPLE 59

Desired Compound

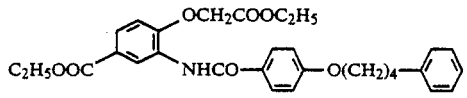

Ethyl 4-ethoxycarbonylmethoxy-3-[p-(4-phenylbutoxy)-benzamido]benzoate

Physicochemical Properties i) Melting point: 93°-94° C.
ii) Elemental analysis for $C_{30}H_{33}NO_7$

|  | C % | H % | N % |
|---|---|---|---|
| Calcd. | 69.35 | 6.40 | 2.70 |
| Found | 69.30 | 6.45 | 2.63 |

Starting compound: Compound of Reference Example 27 + $BrCH_2COOC_2H_5$

EXAMPLE 60

Desired compound

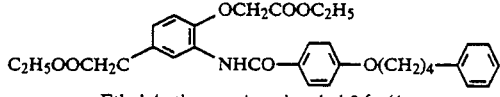

Ethyl 4-ethoxycarbonylmethyl-2-[p-(4-phenylbutoxy)-benzamido]phenoxyacetate

Physicochemical Properties i) Oily product
ii) Elemental analysis for $C_{31}H_{35}NO_7$

|  | N % |
|---|---|
| Calcd. | 2.62 |

-continued

| | N % |
|---|---|
| Found | 2.54 |

Starting compound: Compound of Reference Example 33+BrCH₂COOC₂H₅

EXAMPLE 61

Desired Compound

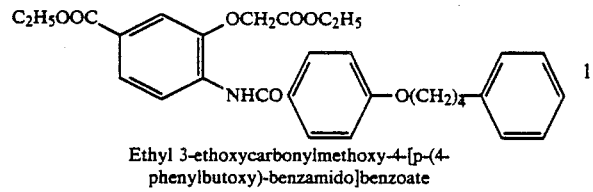

Ethyl 3-ethoxycarbonylmethoxy-4-[p-(4-phenylbutoxy)-benzamido]benzoate

Physicochemical Properties i) Melting point: 113°–114° C.
ii) Elemental analysis for $C_{30}H_{33}NO_7$

| | C % | H % | N % |
|---|---|---|---|
| Calcd. | 69.35 | 6.40 | 2.70 |
| Found | 69.19 | 6.53 | 2.75 |

Starting compound: Compound of Reference Example 34+BrCH₂COOC₂H₅

EXAMPLE 62

Desired Compound

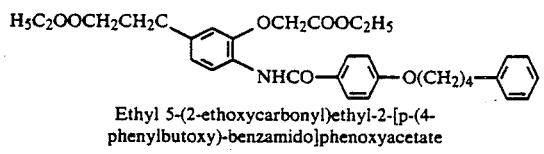

Ethyl 5-(2-ethoxycarbonyl)ethyl-2-[p-(4-phenylbutoxy)-benzamido]phenoxyacetate

Physicochemical Properties i) Melting point: 86°–88° C.
ii) Elemental analysis for $C_{32}H_{37}NO_7$

| | C % | H % | N % |
|---|---|---|---|
| Calcd. | 70.18 | 6.81 | 2.56 |
| Found | 70.19 | 6.87 | 2.57 |

Starting compound: Compound of Reference Example 36+BrCH₂COOC₂H₅

EXAMPLE 63

Desired Compound

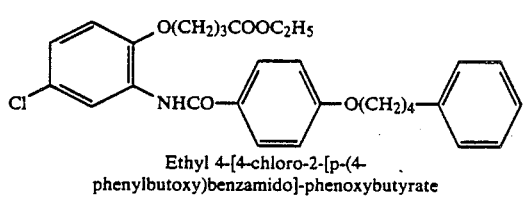

Ethyl 4-[4-chloro-2-[p-(4-phenylbutoxy)benzamido]-phenoxybutyrate

Physicochemical Properties i) Melting point: 87°–88° C.
ii) Elemental analysis for $C_{29}H_{32}NO_5Cl$

| | C % | H % | N % |
|---|---|---|---|
| Calcd. | 68.29 | 6.32 | 2.75 |
| Found | 68.06 | 6.30 | 2.75 |

Starting compound

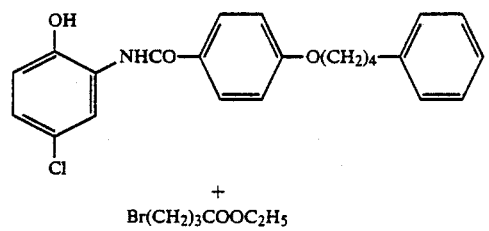

+
Br(CH₂)₃COOC₂H₅

EXAMPLE 64

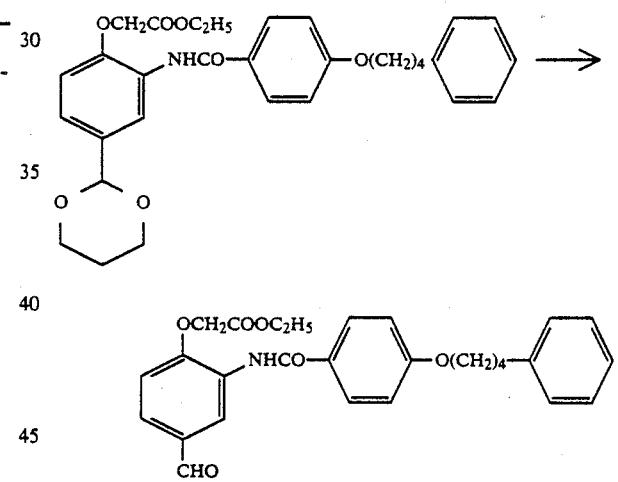

In 200 ml of acetone was dissolved 8.69 g of ethyl 4-(1,3-dioxan-2-yl)-2-[p-(4-phenylbutoxy)benzamido]-phenoxyacetate obtained in Reference Example 41. To the solution was added 6 ml of 6% hydrochloric acid. The mixture was stirred at room temperature for 2 hours. After adding 30 ml of water thereto, the mixture was cooled and the precipitated crystals were taken by filtration, washed with 50% acetone to obtain 6.0 g of ethyl 4-formyl-2-[p-(4-phenylbutoxy)benzamido]-phenoxyacetate.

Melting point: 109°–110° C.
Elemental analysis for $C_{28}H_{29}NO_6$

| | C % | H % | N % |
|---|---|---|---|
| Calcd. | 70.72 | 6.15 | 2.95 |
| Found | 70.77 | 6.05 | 2.93 |

EXAMPLE 65

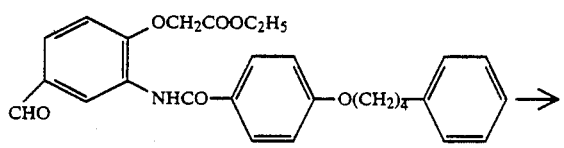

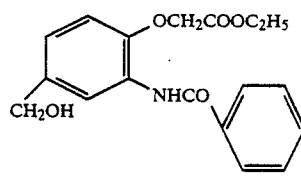

Under ice cooling 0.2 g of sodium borohydride was added to a mixture of 2.8 g of ethyl 4-formyl-2-[p-(4-phenylbutoxy)benzamido]phenoxyacetate obtained in Reference Example 64 and 30 ml of ethanol. The mixture was stirred for 2 hours and 50 ml of ethyl acetate was added thereto. The mixture was rendered acidic with diluted hydrochloric acid. The ethyl acetate layer was fractionated, washed with water, dried over anhydrous magnesium sulfate and concentrated under reduced pressure. The residue was recrystallized from ethanol to obtain 2.06 g of ethyl 4-hydroxymethyl-2-[p-(4-phenylbutoxy)benzamido]phenoxyacetate.

Melting point: 101°–104° C.
Elemental analysis for $C_{28}H_{31}NO_6$

|  | C % | H % | N % |
|---|---|---|---|
| Calcd. | 70.42 | 6.54 | 2.93 |
| Found | 70.25 | 6.51 | 2.85 |

EXAMPLE 66

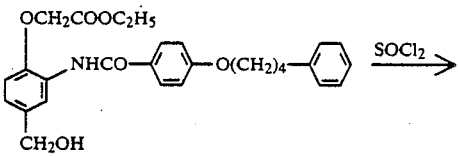

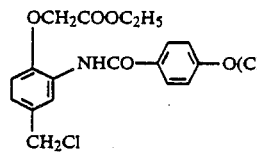

Under ice cooling 260 mg of thionyl chloride was added to a solution of 1 g of ethyl 4-hydroxymethyl-2-[p-(4-phenylbutoxy)benzamido]phenoxyacetate obtained in Reference Example 65 in 20 ml of benzene and 20 ml of methylene chloride. After stirring at room temperature for 30 minutes, 60 ml of toluene was added to the reaction mixture. The mixture was washed with chilled water, dried over anhydrous magnesium sulfate and concentrated under reduced pressure. The residue was recrystallized from toluene-n-hexane to obtain 0.76 mg of ethyl 4-chloroxymethyl-2-[p-(4-phenylbutoxy)-benzamido]phenoxyacetate.

Melting point: 115°–117° C.
Elemental analysis for $C_{28}H_{30}NO_5Cl$

|  | C % | H % | N % | Cl % |
|---|---|---|---|---|
| Calcd. | 67.80 | 6.10 | 2.82 | 7.15 |
| Found | 67.87 | 6.13 | 2.79 | 7.27 |

EXAMPLE 67

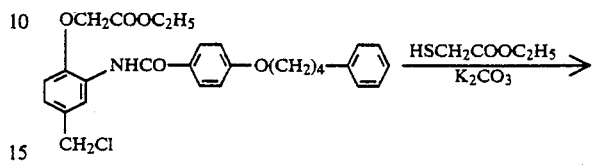

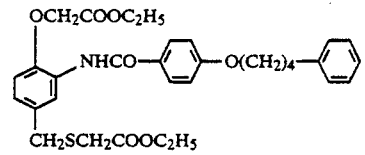

A mixture of 200 mg of ethyl 4-chloroxymethyl-2-[p-(4-phenylbutoxy)benzamido]phenoxyacetate obtained in Reference Example 66, 50 mg of ethyl thioacetate, 60 mg of anhydrous potassium carbonate and 5 ml of N,N-dimethylformamide was stirred at room temperature for 1 hour. After adding 20 ml of toluene thereto, the mixture was washed with water, dried over anhydrous magnesium sulfate and concentrated under reduced pressure. The residue was subjected to silica gel column chromatography (silica gel: 30 ml), eluted with a toluene-ethylacetate (9:1) mixture to obtain 170 mg of ethyl 4-[(ethoxycarbonylmethylthio)methyl]-2-[p-(4-phenylbutoxy)benzamido]phenoxyacetate.

Melting point: 56°–57° C.
Elemental analysis for $C_{32}H_{37}NO_7S$

|  | C % | H % | N % |
|---|---|---|---|
| Calcd. | 66.30 | 6.43 | 2.42 |
| Found | 66.04 | 6.43 | 2.31 |

EXAMPLE 68

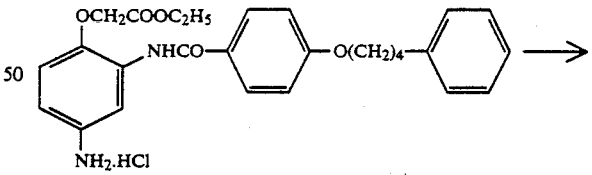

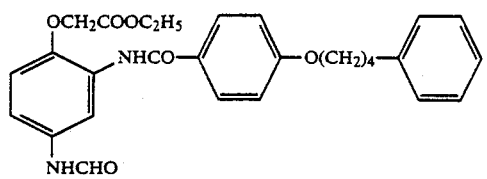

To a mixture of 200 mg of ethyl 4-amino-2-[p-(4-phenylbutoxy)benzamido]phenoxyacetate hydrochloride and 3 ml of pyridine was added 1 ml of formic acid-acetic anhydride (3:5 v/v) mixture followed by stirring at room temperature overnight. To the reaction mixture was added 40 ml of ethyl acetate. The mixture was rendered acidic with diluted hydrochloric acid and then separated. The ethyl acetate layer was washed with water, dried over anhydrous magnesium sulfate and concentrated under reduced pressure. The residue was recrystallized from isopropyl alcohol to obtain 130 mg of ethyl 4-formylamido-2-[p-(4-phenylbutoxy)benzamido]phenoxyacetate.

Melting point: 112°-114° C.

Elemental analysis for $C_{28}H_{30}N_2O_6$

|  | C % | H % | N % |
|---|---|---|---|
| Calcd. | 68.56 | 6.16 | 5.71 |
| Found | 68.43 | 6.31 | 5.62 |

EXAMPLE 69

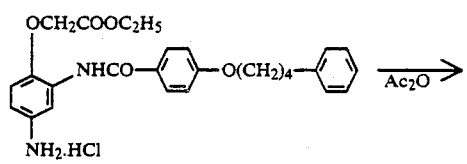

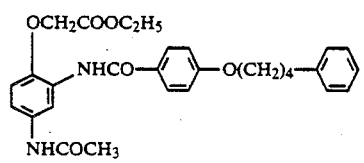

Under ice cooling 1 ml of acetic anhydride was added to a mixture of 200 mg of ethyl 4-amino-2-[p-(4-phenylbutoxy)benzamido]phenoxyacetate hydrochloride and 5 ml of pyridine followed by stirring at room temperature overnight. The reaction mixture was treated similarly to Example 68 to obtain 150 mg of ethyl 4-acetamido-2-[p-(4-phenylbutoxy)benzamido]phenoxyacetate.

Melting point: 130°-132° C.

Elemental analysis for $C_{29}H_{32}N_2O_6$

|  | C % | H % | N % |
|---|---|---|---|
| Calcd. | 69.03 | 6.39 | 5.55 |
| Found | 68.89 | 6.37 | 5.43 |

EXAMPLE 70

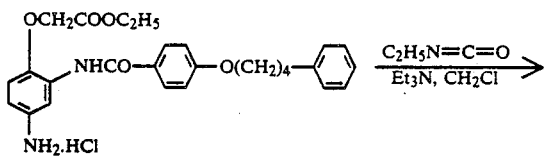

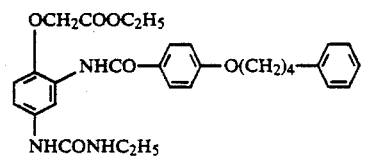

To a mixture of 200 mg of ethyl 4-amino-2-[p-(4-phenylbutoxy)benzamido]phenoxyacetate hydrochloride, 40.5 mg of triethylamine and 5 ml of methylene chloride was added 30 mg of ethyl isocyanate followed by stirring at room temperature overnight. The reaction mixture was treated in a manner similar to Example 68 to obtain 130 mg of ethyl 4-(3-ethylureido)-2-[p-(4-phenylbutoxy)benzamido]phenoxyacetate.

Melting point: 170°-172° C.

Elemental analysis for $C_{30}H_{35}N_3O_6$

|  | C % | H % | N % |
|---|---|---|---|
| Calcd. | 67.53 | 6.61 | 7.87 |
| Found | 67.59 | 6.63 | 7.80 |

EXAMPLE 71

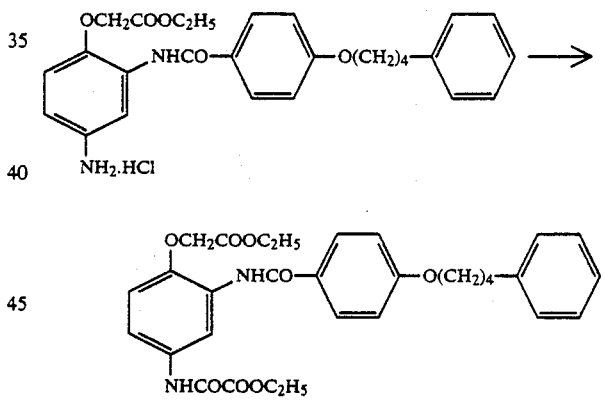

A mixture of 1 ml of ethyl oxalyl chloride and 1 ml of methylene chloride was added to a mixture of 200 mg of ethyl 4-amino-2-[p-(4-phenylbutoxy)benzamido]phenoxyacetate hydrochloride and 5 ml of pyridine at temperatures lower than −30° C. followed by stirring at room temperature overnight. The reaction mixture was treated in a manner similar to Example 68 to obtain 200 mg of oily ethyl 4-ethoxalylamido-2-[p-(4-phenylbutoxy)benzamido]phenoxyacetate.

Nuclear magnetic resonance spectra: (CDCl$_3$, internal standard: TMS, ppm) 1.1-1.6(m, 6H), 1.6-2.0(m, 4H), 2.5-2.8(m, 2H), 3.8-4.1 (m, 2H), 4.1-4.5(m, 4H), 4.58(s, 2H), 6.6-7.8(12H)

EXAMPLE 72

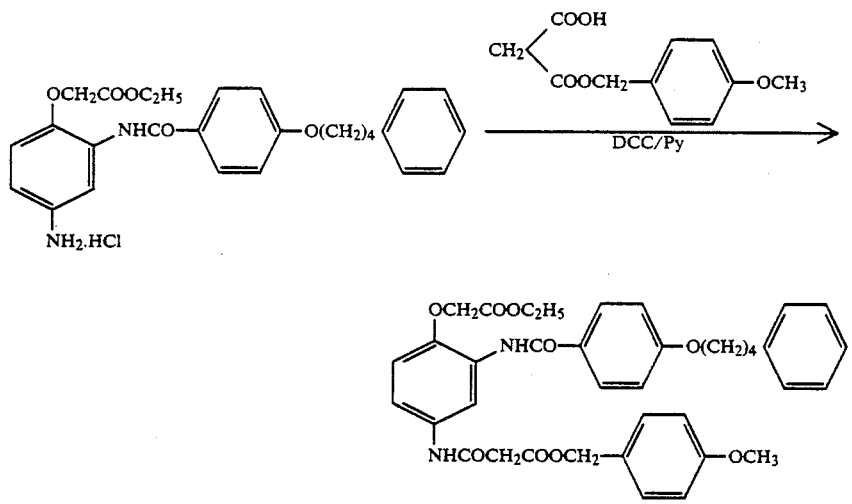

To a mixture of 200 mg of ethyl 4-amino-2-[p-(4-phenylbutoxy)benzamido]phenoxyacetate hydrochloride, 107 mg of mono-p-methoxybenzyl malonate and 5 ml of pyridine was added 90 mg of dicyclohexylcarbodiimide. The mixture was stirred at room temperature overnight. The reaction mixture was treated in a manner similar to Example 68. Thereafter the system was applied to silica gel column chromatography and eluted with a toluene-ethyl acetate (4:1) mixture to obtain 110 mg of caramel-like ethyl 4-(p-methoxybenzyloxycarbonyl)acetamido-2-[p-(4-phenylbutoxy)benzamido]-phenoxyacetate.

Nuclear magnetic resonance spectra: (CDCl$_3$, internal standard: TMS, ppm) 1.18(t,3H), 1.5-2.0(m, 4H), 2.5-2.8(m, 2H), 3.46(s, 2H), 3.72(s, 3H), 4.9-4.2(m, 2H), 4.16(q, 2H), 4.82(s, 2H), 5.06(s, 2H), 6.8-8.3(16H)

EXAMPLE 73

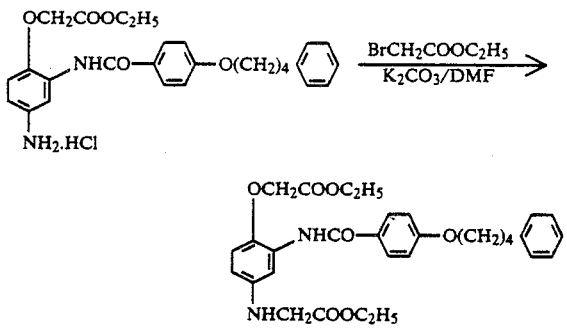

A mixture of 200 mg of ethyl 4-amino-2-[p-(4-phenylbutoxy)benzamido]phenoxyacetate hydrochloride, 70.4 mg of ethyl bromoacetate, 114 mg of anhydrous potassium carbonate and 5 ml of N,N-dimethylformamide was stirred at room temperature overnight. To the reaction mixture was added 30 ml of ethyl acetate. After washing with water, the system was dried over anhydrous magnesium sulfate and concentrated under reduced pressure. The residue was applied to silica gel column chromatography and eluted with a toluene-ethyl acetate (4:1) mixture to obtain 140 mg of ethyl 4-(ethoxycarbonylmethylamino)-2-[p-(4-phenylbutoxy)benzamido]phenoxyacetate.

Melting point: 61°-63° C.

Elemental analysis for C$_{31}$H$_{36}$N$_2$O$_7$

|        | C %   | H %  | N %  |
|--------|-------|------|------|
| Calcd. | 67.87 | 6.61 | 5.11 |
| Found  | 67.74 | 6.56 | 5.11 |

EXAMPLE 74

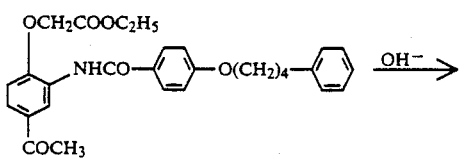

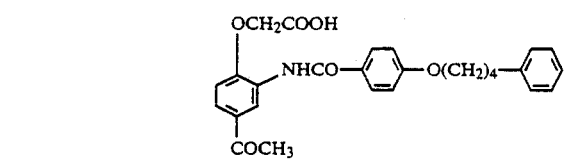

A 1N sodium hydroxide aqueous solution was added to a mixture of 0.5 g of ethyl 4-acetyl-2-[p-(4-phenylbutoxy)benzamido]phenoxyacetate obtained in Example 53, 5 ml of methanol and 5 ml of tetrahydrofuran and the mixture was stirred at room temperature for 2 hours. To the reaction mixture was added 10 ml of water. The mixture was concentrated under reduced pressure to remove methanol and tetrahydrofuran. Diluted hydrochloric acid was added to the residue to render acidic. The formed crystals were taken by filtration and recrystallized from isopropyl alcohol to obtain 0.39 g of 4-acetyl-2-[p-(4-phenylbutoxy)benzamido]phenoxyacetic acid.

Melting point 186°-188° C.

Elemental analysis for C$_{27}$H$_{27}$NO$_6$

|        | C %   | H %  | N %  |
|--------|-------|------|------|
| Calcd. | 70.27 | 5.90 | 3.03 |
| Found  | 70.07 | 5.73 | 3.02 |

Compounds of Examples 75 through 92 were obtained following the same procedure.

EXAMPLE 75

Desired Compound

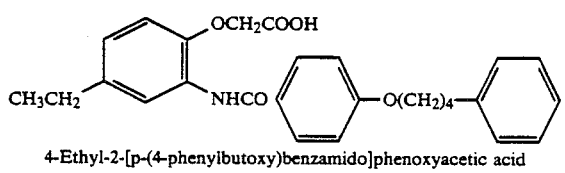

4-Ethyl-2-[p-(4-phenylbutoxy)benzamido]phenoxyacetic acid

Physicochemical Properties i) Melting point: 129°~132° C.
ii) Elemental analysis for $C_{27}H_{29}NO_5$

|  | C % | H % | N % |
|---|---|---|---|
| Calcd. | 72.46 | 6.53 | 3.13 |
| Found | 72.33 | 6.65 | 3.09 |

Starting Compound: Compound of Example 55

EXAMPLE 76

Desired Compound

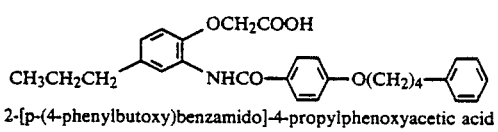

2-[p-(4-phenylbutoxy)benzamido]-4-propylphenoxyacetic acid

Physicochemical Properties i) Melting point: 109°~112° C.
ii) Elemental analysis for $C_{28}H_{31}NO_5$

|  | N % |
|---|---|
| Calcd. | 3.03 |
| Found | 3.01 | iii) Nuclear magnetic resonance spectra (CDCl$_3$, TMS internal standard, ppm): 0.90(t,3H), 1.4–2.0(6H), 2.4–2.8(4H), 3.8–4.1(2H), 4.70(s, 2H), 6.7–7.0(4H), 7.0–7.4(5H), 7.8–8.0(2H), 8.15(d, 1H), 8.62(s, 1H), 8.91(s, 1H)

Starting Compound: Compound of Example 56

EXAMPLE 77

Desired Compound

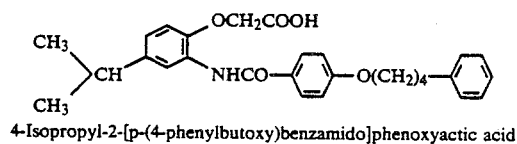

4-Isopropyl-2-[p-(4-phenylbutoxy)benzamido]phenoxyactic acid

Physicochemical Properties i) Melting point: 117°~119° C.
ii) Elemental analysis for $C_{28}H_{31}NO_5$

|  | C % | H % | N % |
|---|---|---|---|
| Calcd. | 72.86 | 6.77 | 3.03 |
| Found | 73.05 | 6.91 | 3.04 |

Starting Compound: Compound of Example 57

EXAMPLE 78

Desired Compound

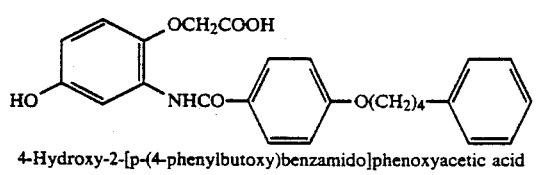

4-Hydroxy-2-[p-(4-phenylbutoxy)benzamido]phenoxyacetic acid

Physicochemical Properties i) Melting point: 198°~199° C.
ii) Elemental analysis for $C_{25}H_{25}NO_6$

|  | C % | H % | N % |
|---|---|---|---|
| Calcd. | 68.95 | 5.79 | 3.22 |
| Found | 69.01 | 5.99 | 3.13 |

Starting Compound: Compound of Example 42

EXAMPLE 79

Desired Compound

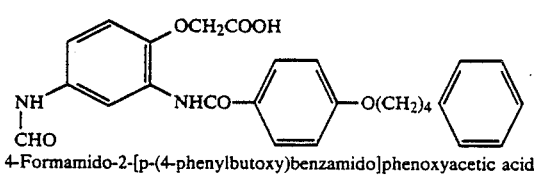

4-Formamido-2-[p-(4-phenylbutoxy)benzamido]phenoxyacetic acid

Physicochemical Properties i) Melting point: 78°~80° C.
ii) Elemental analysis for $C_{26}H_{26}N_2O_6$

|  | N % |
|---|---|
| Calcd. | 6.06 |
| Found | 5.99 |

Starting Compound: Compound of Example 68

EXAMPLE 80

Desired Compound

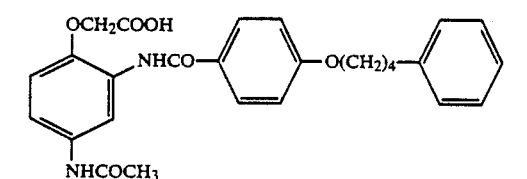

4-Acetamido-2-[p-(4-phenylbutoxy)benzamido]phenoxyacetic acid

Physicochemical Properties i) Melting point: 184°~186° C.

ii) Elemental analysis for $C_{27}H_{28}N_2O_6$

|  | C % | H % | N % |
|---|---|---|---|
| Calcd. | 68.05 | 5.92 | 5.88 |
| Found | 67.77 | 5.96 | 5.79 |

Starting Compound: Compound of Example 69

EXAMPLE 81

Desired Compound

4-Oxalimido-2-[p-(4-phenylbutoxy)benzamido]phenoxy-acetic acid

Physicochemical Properties i) Melting point: 206°~207° C. (decomposed)
ii) Elemental analysis for $C_{27}H_{26}N_2O_8 \cdot 1/2H_2O$

|  | C % | H % | N % |
|---|---|---|---|
| Calcd. | 63.57 | 5.22 | 5.49 |
| Found | 63.63 | 5.21 | 5.44 |

Starting Compound: Compound of Example 71

EXAMPLE 81

Desired Compound

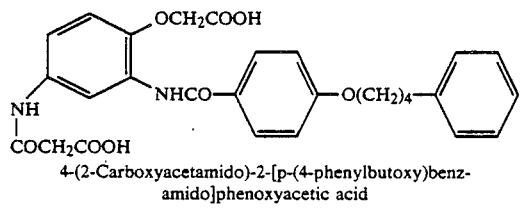

4-(2-Carboxyacetamido)-2-[p-(4-phenylbutoxy)benzamido]phenoxyacetic acid

Physicochemical Properties i) Melting point: 179°~181° C. (decomposed)
ii) Elemental analysis for $C_{28}H_{28}N_2O_8$

|  | C % | H % | N % |
|---|---|---|---|
| Calcd. | 64.61 | 5.42 | 5.38 |
| Found | 64.67 | 5.39 | 5.32 |

Starting Compound: Compound of Example 72

EXAMPLE 83

Desired Compound

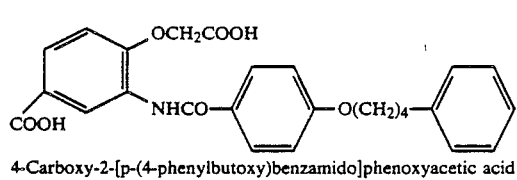

4-Carboxy-2-[p-(4-phenylbutoxy)benzamido]phenoxyacetic acid

Physicochemical Properties i) Melting point: 244°~246° C.
ii) Elemental analysis for $C_{26}H_{25}NO_7$

|  | C % | H % | N % |
|---|---|---|---|
| Calcd. | 67.38 | 5.44 | 3.02 |
| Found | 67.33 | 5.48 | 3.03 |

Starting Compound: Compound of Example 59

EXAMPLE 84

Desired Compound

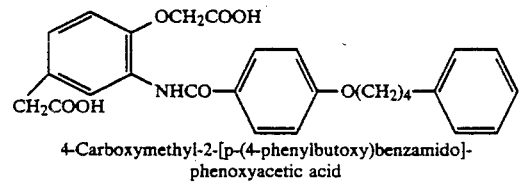

4-Carboxymethyl-2-[p-(4-phenylbutoxy)benzamido]-phenoxyacetic acid

Physicochemical Properties i) Melting point: 210°~213° C.
ii) Elemental analysis for $C_{27}H_{27}NO_7$

|  | C % | H % | N % |
|---|---|---|---|
| Calcd. | 67.91 | 5.70 | 2.93 |
| Found | 67.45 | 5.69 | 2.92 |

Starting Compound: Compound of Example 60

EXAMPLE 85

Desired Compound

4-Formyl-2-[p-(4-phenylbutoxy)benzamido]phenoxyacetic acid

Physicochemical Properties i) Melting point: 151°~152° C.
ii) Elemental analysis for $C_{26}H_{25}NO_6$

|  | C % | H % | N % |
|---|---|---|---|
| Calcd. | 69.79 | 5.63 | 3.13 |
| Found | 69.79 | 5.54 | 3.11 |

Starting Compound: Compound of Example 64

EXAMPLE 86

Desired Compound

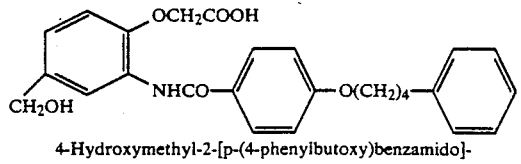

4-Hydroxymethyl-2-[p-(4-phenylbutoxy)benzamido]-

-continued
phenoxyacetic acid

Physicochemical Properties i) Melting point: 138°~139° C.
ii) Elemental analysis for $C_{26}H_{27}NO_6$

|  | C % | H % | N % |
|---|---|---|---|
| Calcd. | 69.47 | 6.05 | 3.12 |
| Found | 69.34 | 5.81 | 3.05 |

Starting Compound: Compound of Example 65

EXAMPLE 87

Desired Compound

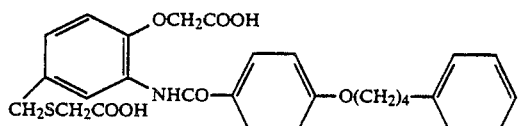

4-Carboxymethylthiomethyl-2-[p-(4-phenylbutoxy)-
benzamido]phenoxyacetic acid

Physicochemical Properties i) Melting point: 139°~141° C.
ii) Elemental analysis for $C_{28}H_{29}NO_7S$

|  | N % |
|---|---|
| Calcd. | 2.68 |
| Found | 2.57 |

Starting Compound: Compound of Example 67

EXAMPLE 88

Desired Compound

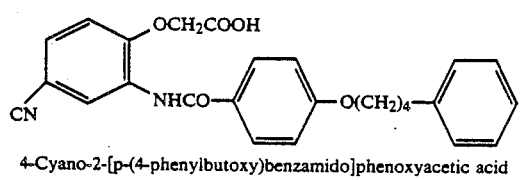

4-Cyano-2-[p-(4-phenylbutoxy)benzamido]phenoxyacetic acid

Physicochemical Properties i) Melting point: 148°~149° C.
ii) Elemental analysis for $C_{26}H_{24}N_2O_5$

|  | C % | H % | N % |
|---|---|---|---|
| Calcd. | 70.26 | 5.44 | 6.30 |
| Found | 70.14 | 5.44 | 6.12 |

Starting Compound: Compound of Example 58

EXAMPLE 89

Desired Compound

4-Bromo-2-[p-(4-phenylbutoxy)benzamido]phenoxyacetic acid

Physicochemical Properties i) Melting point: 163°~165° C.
ii) Elemental analysis for $C_{25}H_{24}NO_5Br$

|  | C % | H % | N % | Br % |
|---|---|---|---|---|
| Calcd. | 60.25 | 4.85 | 2.81 | 16.03 |
| Found | 60.15 | 4.99 | 2.75 | 16.02 |

Starting Compound: Compound of Example 54

EXAMPLE 90

Desired Compound

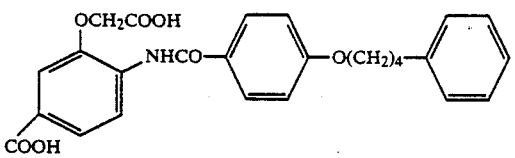

5-Carboxy-2-[p-(4-phenylbutoxy)benzamido]phenoxyacetic acid

Physicochemical Properties i) Melting point: 235°~237.5° C.
ii) Elemental analysis for $C_{26}H_{25}NO_7$

|  | C % | H % | N % |
|---|---|---|---|
| Calcd. | 67.38 | 5.44 | 3.02 |
| Found | 67.06 | 5.53 | 3.10 |

Starting Compound: Compound of Example 61

EXAMPLE 91

Desired Compound

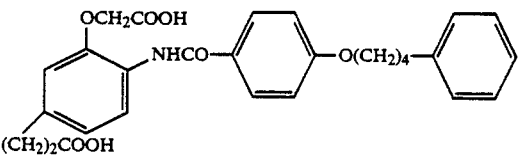

5-(2-Carboxy)ethyl-2-[p-(4-phenylbutoxy)benzamido]-
phenoxyacetic acid

Physicochemical Properties i) Melting point: 147°~149° C.
ii) Elemental analysis for $C_{28}H_{29}NO_7 \cdot 0.3H_2O$

|  | C % | H % | N % |
|---|---|---|---|
| Calcd. | 67.68 | 6.00 | 2.82 |

-continued

| | C % | H % | N % |
|---|---|---|---|
| Found | 67.60 | 6.19 | 2.64 |

Starting Compound: Compound of Example 62

EXAMPLE 92

Desired Compound

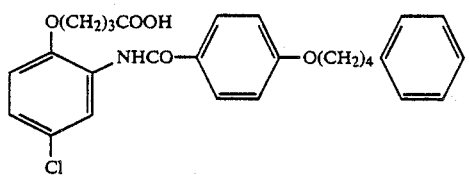

4-[4-Chloro-2-[p-(4-phenylbutoxy)benzamido]phenoxy]-butyric acid

Physicochemical Properties i) Melting point: 118°~119° C.
ii) Elemental analysis for $C_{27}H_{28}NO_5Cl$

| | C % | H % | N % |
|---|---|---|---|
| Calcd. | 67.28 | 5.86 | 2.91 |
| Found | 67.13 | 5.77 | 2.82 |

Starting Compound: Compound of Example 63

EXAMPLE 93

Desired Compound

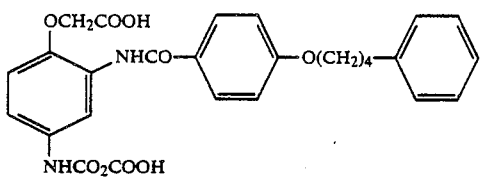

4-Carboxymethylamino-2-[p-(4-phenylbutoxy)benzamido]-phenoxyacetic acid

Physicochemical Properties i) Melting point: 129°~132° C.
ii) Elemental analysis for $C_{27}H_{28}N_2O_7 \cdot 1/2H_2O$

| | C % | H % | N % |
|---|---|---|---|
| Calcd. | 64.66 | 5.83 | 5.59 |
| Found | 64.69 | 5.92 | 5.46 |

Starting Compound: Compound of Example 73

EXAMPLE 94

Desired Compound

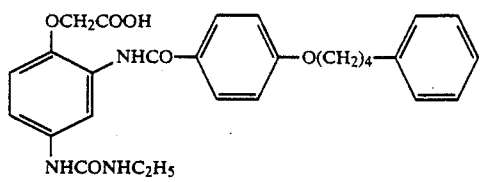

4-(3-Ethylureido)-2-[p-(4-phenylbutoxy)benzamido]-phenoxyacetic acid

Physicochemical Properties i) Melting point: 156° C.
ii) Elemental analysis for $C_{28}H_{31}N_3O_6$

| | C % | H % | N % |
|---|---|---|---|
| Calcd. | 66.52 | 6.18 | 8.31 |
| Found | 66.18 | 6.15 | 8.13 |

Starting Compound: Compound of Example 70

EXAMPLE 95

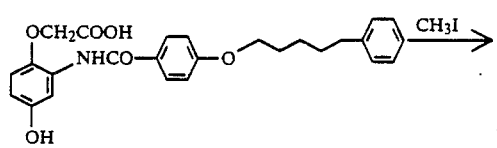

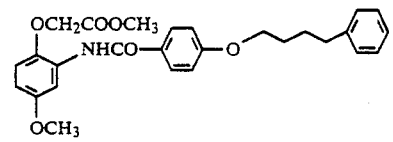

A catalytic amount of tetra-n-butylammonium bromide was added to a mixture of 0.62 g of 4-hydroxy-2-[p-(4-phenylbutoxy)benzamido]phenoxyacetic acid obtained in Example 78, 0.46 g of anhydrous potassium carbonate, 2.47 g of methyl iodide and 10 ml of 2-butanone followed by stirring at 60° C. for 20 hours. The reaction mixture was diluted with ethyl acetate and insoluble materials were filtered off. After the filtrate was washed in order with a 0.02N aqueous sodium hydroxide solution and water and dried over anhydrous magnesium sulfate, the solvent was distilled off. The obtained solid was recrystallized from ethanol to obtain 0.59 g of methyl 4-methoxy-2-[p-(4-phenylbutoxy)benzamido]phenoxyacetate.

Melting point: 91°~93° C.
ii) Elemental analysis for $C_{27}H_{29}NO_6$

| | N % |
|---|---|
| Calcd. | 3.02 |
| Found | 2.98 |

EXAMPLE 96

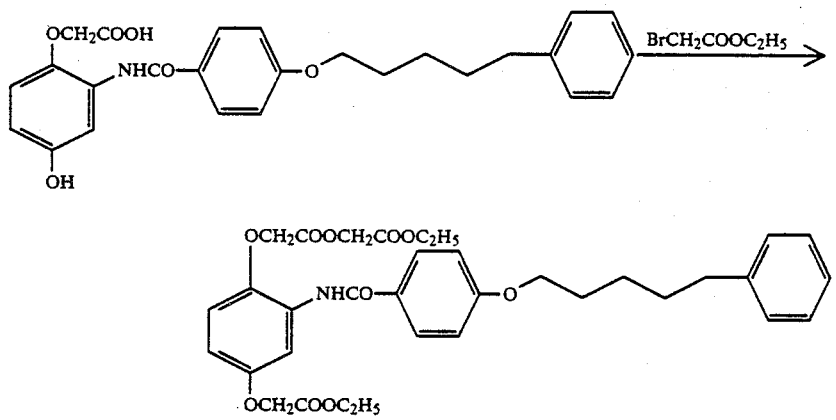

A catalytic amount of tetra-n-butylammonium bromide was added to a mixture of 0.64 g of 4-hydroxy-2-[p-(4-phenylbutoxy)benzamido]phenoxyacetic acid obtained in Example 78, 0.50 g of anhydrous potassium carbonate, 0.60 g of ethyl bromoacetate and 8 ml of 2-butanone followed by stirring at 60° C. for 4 hours. The reaction mixture was diluted with ethyl acetate and insoluble materials were filtered off. After the filtrate was washed with water and dried over anhydrous magnesium sulfate, the solvent was distilled off. The obtained solid was recrystallized from ethanol to obtain 0.83 g of ethyl [[4-ethoxycarbonylmethoxy-2-[p-(4-phenylbutoxy)benzamido] phenoxy]acetoxy]acetate.

Melting point: 64° C.
Elemental analysis for $C_{33}H_{37}NO_{10}$

|  | C % | H % | N % |
|---|---|---|---|
| Calcd. | 65.23 | 6.14 | 2.31 |
| Found | 65.00 | 5.96 | 2.23 |

EXAMPLE 97

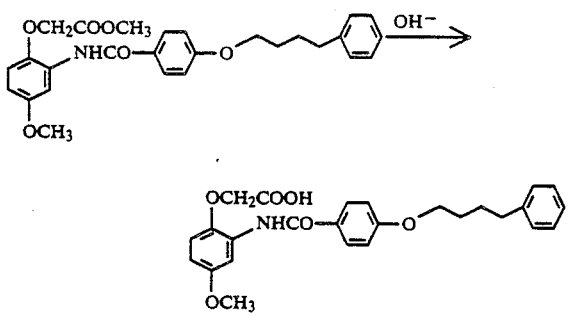

In 25 ml of 90% methanol was suspended 0.54 g of methyl 4-methoxy-2-[p-(4-phenylbutoxy)benzamido]phenoxyacetate obtained in Example 95. To the suspension wad added 10 ml of a 1N sodium hydroxide aqueous solution followed by stirring at 60° C. for 2 hours. The reaction mixture was diluted with 50 ml of water and the system was rendered acidic with 7 ml of 2N hydrochloric acid. Extraction was performed with ethyl acetate. After the organic layer was washed water and dried over anhydrous magnesium sulfate, the solvent was distilled off. The obtained solid was recrystallized from isopropyl alcohol to obtain 0.4 g of 4-methoxy-2-[p-(4-phenylbutoxy)benzamido]phenoxyacetic acid.

Melting point: 139°~141° C.
ii) Elemental analysis for $C_{26}H_{27}NO_6$

|  | C % | H % | N % |
|---|---|---|---|
| Calcd. | 69.47 | 6.05 | 3.12 |
| Found | 69.33 | 6.13 | 3.03 |

EXAMPLE 98

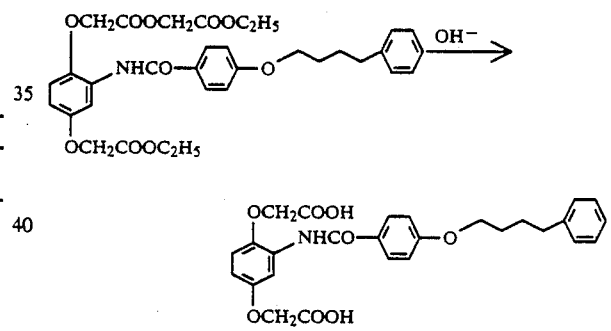

Ethyl [[4-ethoxycarbonymethoxy-2-[p-(4-phenylbutoxy)benzamido]phenoxy]acetoxy]acetate, 0.77 g, obtained in Example 96 was used as a starting compound and treated in a manner similar to Example 97 to obtain 0.57 g of [2-[p-(4-phenylbutoxy)benzamido]-1,4-phenylenedioxy]diacetic acid.

Melting point: 211°~214° C.
ii) Elemental analysis for $C_{27}H_{27}NO_8$

|  | C % | H % | N % |
|---|---|---|---|
| Calcd. | 65.71 | 5.51 | 2.84 |
| Found | 65.74 | 5.51 | 2.77 |

EXAMPLE 99

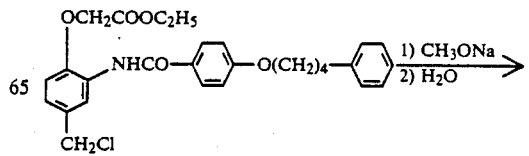

-continued

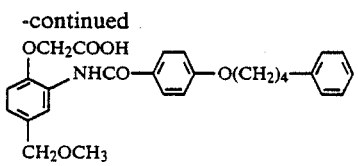

To a sodium methoxide-methanol solution obtained from 100 mg of metallic sodium and 5 ml of methanol was added 200 mg of ethyl 4-chloromethyl-2-[p-(4-phenylbutoxy)benzamido]phenoxyacetate obtained in Example 66. The mixture was stirred at room temperature overnight. To the reaction mixture was added 1 ml of water and stirred for 1 hour. After rendering acidic with diluted hydrochloric acid, the system was concentrated under reduced pressure. To the residue was added 10 ml of water. The formed crystals were filtered and recrystallized from isopropyl alcohol to obtain 100 mg of 4-methoxymethyl-2-[p-(4-phenylbutoxy)benzamido]phenoxyacetic acid.

Melting point: 126°~129° C.
ii) Elemental analysis for $C_{26}H_{25}NO_6$

|  | C % | H % | N % |
|---|---|---|---|
| Calcd. | 69.79 | 5.63 | 3.13 |
| Found | 69.79 | 5.54 | 3.11 |

EXAMPLE 100

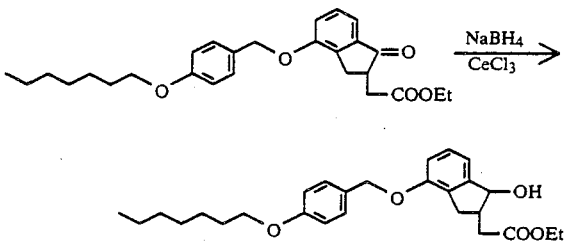

To a solution of 30 mg of cerous chloride heptahydrate in 8 ml of methanol was dissolved 350 mg of ethyl 4-(p-heptyloxybenzyloxy)-indan-1-one-2-acetate obtained in Reference Example 43. The mixture was cooled to −10° C. There was added 300 mg of sodium borohydride followed by stirring for 30 minutes. Water was added and the temperature was elevated to room temperature. The product was extracted with ethyl acetate. The ethyl acetate layer was washed twice with a saturated saline aqueous solution, dried over anhydrous magnesium sulfate and concentrated under reduced pressure to obtain 390 mg of ethyl 1-hydroxy-4-(p-heptyloxybenzyloxy)indan-2-acetate.

i) Oily product
ii) Nuclear magnetic resonance spectra (CDCl₃, internal standard; TMS, ppm) 0.8–1.0(3H), 1.25, 1.28(3H by joining, each of them is t), 1.2–1.45(8H), 1.6–1.9(2H), 2.3–4.4(5H), 3.96 (2H, t), 4.15, 4.21(2H by joining, each of them is q, 7:4), 5.00(2H, s), 5.20(1H, w/2=11Hz), 6.8–7.4(7H).

EXAMPLE 101

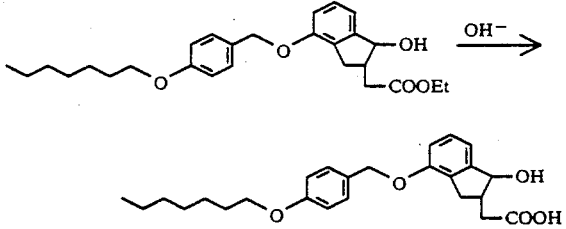

In 10 ml of methanol was dissolved 380 mg of ethyl 1-hydroxy-4-(p-heptyloxybenzyloxy)-2-indaneacetate obtained in Example 100 and, 2.5 ml of a 5% sodium hydroxide solution was added thereto followed by stirring at room temperature for 8 hours. The system was rendered acidic with 20% hydrochloric acid and extracted with ethyl acetate. The ethyl acetate layer was washed subsequently with water and then a saturated saline aqueous solution, dried over anhydrous magnesium sulfate and concentrated under reduced pressure. The crystalline residue was recrystallized from ethyl acetate-hexane to obtain 230 mg of 1-hydroxy-4-(p-heptyloxybenzyloxy)-2-indaneacetic acid.

i) Melting point: 180° C.
ii) Elemental analysis for $C_{25}H_{32}O_5$

|  | C % | H % |
|---|---|---|
| Calcd. | 72.79 | 7.82 |
| Found | 72.66 | 7.98 |

EXAMPLE 102

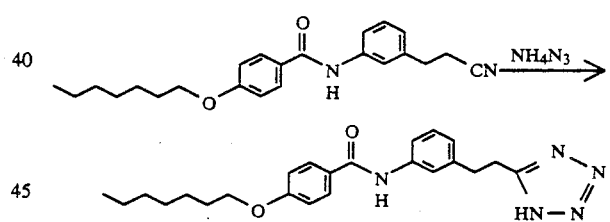

In 5 ml of N,N-dimethylformamide was dissolved 630 mg of 3-[m-[p-heptyloxy)benzamido]phenyl]propionitrile obtained in Example 44. To the solution were added 340 mg of sodium azide and 280 mg of ammonium chloride. The mixture was heated at 130° C. Four hours and 16 hours after, the same amounts of sodium azide and ammonium chloride were added to the system followed by heating 20 hours. Water was added to the reaction mixture and the formed crystalline solid was collected by suction. After washing with water and drying, the solid was recrystallized from methanol-ethyl acetate to obtain 540 mg of 4-heptyloxy-3'-[2-(5-tetrazolyl)ethyl]benzanilide.

i) Melting point: 164°~165° C.
ii) Elemental analysis for $C_{23}H_{29}N_5O_2$

|  | C % | H % | N % |
|---|---|---|---|
| Calcd. | 67.79 | 7.17 | 17.19 |
| Found | 67.96 | 7.13 | 16.91 |

EXAMPLE 103

(Tablet)

| Compound of Example 40 | 30 mg |
|---|---|
| Lactose | 104 mg |
| Corn starch | 57 mg |
| Hydroxypropyl cellulose | 4 mg |
| Calcium carboxymethyl cellulose | 4 mg |
| Magnesium stearate | 1 mg |
| total | 200 mg |

After uniformly mixing 30 g of Compound of Example 40, 104 g of lactose and 57 g of corn starch, 40 ml of a 10% (w/w) aqueous solution of hydroxypropyl cellulose was added to the mixture and the resulting mixture was granulated by a wet granulation method. The granules thus obtained were mixed with 4 g of calcium carboxymethyl cellulose and 1 g of magnesium stearate and the mixture was press-tabletted into tablets (200 mg per tablet).

EXAMPLE 104

(capsule)

| Compound of Example 40 | 30 mg |
|---|---|
| Crystalline cellulose | 40 mg |
| Crystalline lactone | 129 mg |
| Magnesium stearate | 1 mg |
| total | 200 mg |

The above components each in an amount 1000 times the foregoing amount were mixed and then filled in gelatin capsule to provide capsules (200 mg per capsule).

EXAMPLE 105

After dissolving 0.1 g of Compound of Example 40 in about 90 ml of a mixture of ethanol, propylene glycol and purified water (30:10:60 in weight ratio), the volume of the solution was adjusted to 100 ml using the aforesaid mixture and 10 ml each of the solution was filled in a definite container followed by sealing to provide a product suitable for administration by an inhalation.

We claim:

1. A compound represented by the general formula (I) or a pharmaceutically acceptable salt thereof:

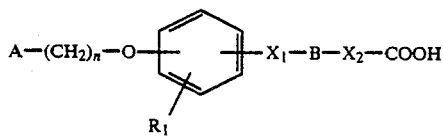

wherein:
A: hydrogen atom or a phenyl group;
n: an integer of 3 to 5;
$R_1$: hydrogen atom or a lower alkyl group;
$X_1$: a group shown by —CO—NH—
B: a group represented by:

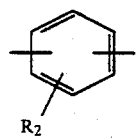

wherein:
$R_2$: a carboxy group, a carboxy lower alkyl group, or a group represented by the formula $$-N\begin{matrix}R_4\\R_5\end{matrix}$$

wherein $R_4$ and $R_5$, which may be the same or different, is a hydrogen atom, a carboxy-lower alkyl group, a lower alkanoyl group, a carboxy-lower alkanoyl group, an oxalyl group, a lower alkoxy oxalyl group or a mono-lower alkylaminocarbonyl group; and $X_2$: a group represented by —O—$Y_4$—; $Y_4$: an alkylene group having 1 to 6 carbon atoms.

2. A compound as claimed in claim 1, wherein A represents a phenyl group, n is an integer of 4 or 5, $R_1$ is a hydrogen atom, $X_1$ is a group shown by —CO—NH—, B is:

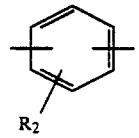

wherein $R_2$ is a carboxy-lower alkyl group or a oxalyl amino group, $X_2$ is —O—$CH_2$.

3. A compound as claimed in claim 1, which is 4-amino-2-[p-(4-phenylbutoxy)benzamido]phenoxyacetic acid.

4. A compound as claimed in claim 1, which is o-[p-(4-phenylbutoxy)benzyloxy]phenoxyacetic acid.

5. A compound as claimed in claim 1, which is o-[3-methoxy-4-(4-phenylbutoxy)styryl]phenoxyacetic acid.

6. A compound as claimed in claim 1, which is o-[o-(4-phenylbutoxy)styryl]phenoxyacetic acid.

7. A compound as claimed in claim 1, which is 4-acetamido-2-[p-(4-phenylbutoxy)benzamido]phenoxyacetic acid.

8. A compound as claimed in claim 1, which is 4-oxalamido-2-[p-(4-phenylbutoxy)benzamido]phenoxyacetic acid.

9. A compound as claimed in claim 1, which is 4-(2-carboxyacetamido)-2-[p-(4-phenylbutoxy)benzamido]-phenoxyacetic acid.

10. A compound as claimed in claim 1, which is 4-formyl-2-[p-(4-phenylbutoxy)benzamido]phenoxyacetic acid.

11. A compound as claimed in claim 1, which is 5-carboxy-2-]p-(4-phenylbutoxy)benzamido]phenoxyacetic acid.

12. A compound as claimed in claim 1, which is 5-(2-carboxy)ethyl-2-[p-(4-phenylbutoxy)benzamido]-phenoxyacetic acid.

13. A compound as claimed in claim 1, which is 4-carboxymethylamino-2-[p-(4-phenylbutoxy)benzamido]-phenoxyacetic acid.

14. A compound as claimed in claim 1, which is 4-(3-ethylureido)-2-[p-(4-phenylbutoxy)benzamido]phenoxyacetic acid.

15. A compound as claimed in claim 1, which is [2-]p-(4-phenylbutoxy)benzamido]-1,4-phenylenedioxy]diacetic acid.

16. A pharmaceutical composition useful for inhibiting the production and release of SRS-A comprised of a pharmaceutically acceptable amount of the compound of claim 1 and a pharmaceutically acceptable carrier.

17. A method for inhibiting the production and release of SRS-A in a subject, which comprises administering to said subject an effective amount for inhibiting the production and release of SRS-A of the pharmaceutical composition of claim 16.

* * * * *